United States Patent
Leguijt et al.

(10) Patent No.: US 10,338,372 B2
(45) Date of Patent: Jul. 2, 2019

(54) CARRIER FLUID COMPOUNDS AND DYE COMPOUNDS FOR ELECTROWETTING APPARATUS

(71) Applicant: Amazon Technologies, Inc., Seattle, WA (US)

(72) Inventors: Robin Leguijt, Eindhoven (NL); Jurriën Mans, Eindhoven (NL); Sukhdip Sandhu, Eindhoven (NL)

(73) Assignee: Amazon Technologies, Inc., Seattle, WA (US)

( * ) Notice: Subject to any disclaimer, the term of this patent is extended or adjusted under 35 U.S.C. 154(b) by 598 days.

(21) Appl. No.: 14/310,484

(22) Filed: Jun. 20, 2014

(65) Prior Publication Data

US 2015/0370062 A1 Dec. 24, 2015

(51) Int. Cl.
*G02B 26/00* (2006.01)
*C09B 1/28* (2006.01)
(Continued)

(52) U.S. Cl.
CPC .......... *G02B 26/005* (2013.01); *C07F 7/0805* (2013.01); *C07F 7/30* (2013.01);
(Continued)

(58) Field of Classification Search
CPC ......... G02B 26/00; G02B 26/005; C07F 7/08; C07F 7/30; C07F 7/0805
(Continued)

(56) References Cited

U.S. PATENT DOCUMENTS 4,578,497 A * 3/1986 Onopchenko ......... C07F 7/0809
556/479
5,782,934 A * 7/1998 Hall ........................ C09B 31/02
534/816
(Continued)

FOREIGN PATENT DOCUMENTS

CN 1344763 A 4/2002
CN 101395495 A 3/2009
(Continued)

OTHER PUBLICATIONS

Robin Leguijt, et al., "Electrowetting Device", U.S. Appl. No. 14/228,776, filed Mar. 28, 2014.
(Continued)

*Primary Examiner* — Bijan Ahvazi
(74) *Attorney, Agent, or Firm* — EIP US LLP

(57) ABSTRACT

Electrowetting apparatus including at least one compound selected from the group consisting of:

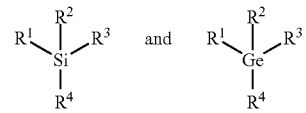

wherein each of $R^1$, $R^2$, $R^3$ and $R^4$ is independently an alkyl group. In examples a fluid includes a dye compound selected from:
(Continued)

US 10,338,372 B2

Page 2

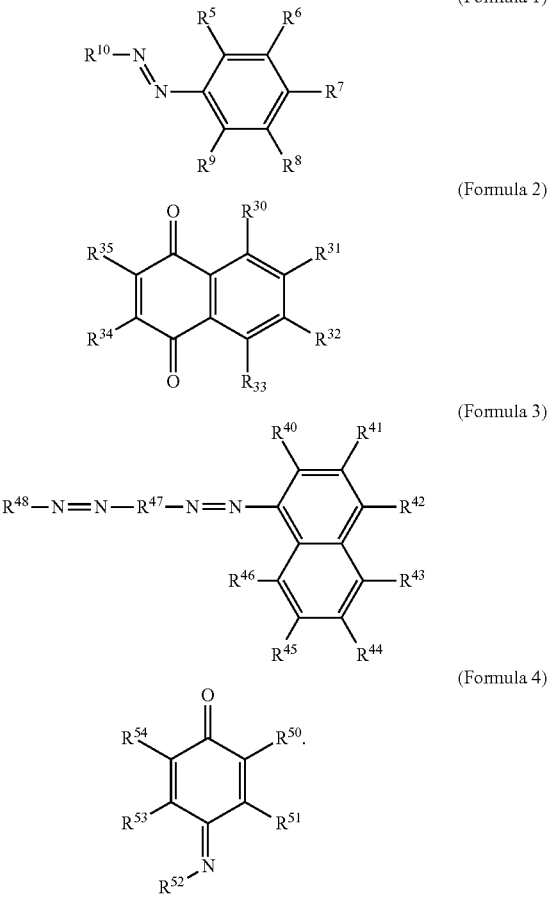

(Formula 1)
(Formula 2)
(Formula 3)
(Formula 4)

24 Claims, 1 Drawing Sheet

(51) Int. Cl.
| | |
|---|---|
| C09B 29/00 | (2006.01) |
| C09B 29/08 | (2006.01) |
| C09B 29/36 | (2006.01) |
| C09B 31/043 | (2006.01) |
| C07F 7/30 | (2006.01) |
| C07F 7/08 | (2006.01) |
| C09B 13/02 | (2006.01) |
| C09B 29/01 | (2006.01) |
| C09B 31/14 | (2006.01) |
| C09B 31/18 | (2006.01) |
| C09B 55/00 | (2006.01) |
| C09B 56/08 | (2006.01) |
| C09B 1/26 | (2006.01) |

(52) U.S. Cl.
CPC ............. C09B 1/26 (2013.01); C09B 1/262 (2013.01); C09B 13/02 (2013.01); C09B 29/0003 (2013.01); C09B 29/081 (2013.01); C09B 31/043 (2013.01); C09B 31/14 (2013.01); C09B 31/18 (2013.01); C09B 55/009 (2013.01); C09B 56/08 (2013.01)

(58) Field of Classification Search
USPC ........ 252/500, 519.21, 586; 359/290; 516/9; 534/573; 556/87, 465
See application file for complete search history.

(56) References Cited

U.S. PATENT DOCUMENTS

| | | | |
|---|---|---|---|
| 2006/0290653 | A1 | 12/2006 | Kawahara et al. |
| 2007/0179200 | A1* | 8/2007 | Liogier D'Ardhuy .. G02B 3/14 516/9 |
| 2008/0225378 | A1* | 9/2008 | Weikert ............... G02B 3/14 359/319 |

FOREIGN PATENT DOCUMENTS

| | | | |
|---|---|---|---|
| CN | 103270445 A | | 8/2013 |
| CN | 106164737 A | | 11/2016 |
| DE | 1273729 | | 7/1968 |
| EP | 1188799 A1 | | 3/2002 |
| GB | 878738 | * | 10/1961 |
| JP | 2009525502 A | | 7/2009 |
| JP | 2014506274 A | | 3/2014 |
| WO | 2005098524 A1 | | 10/2005 |
| WO | 2007088453 A1 | | 8/2007 |
| WO | 2008142086 A1 | | 11/2008 |
| WO | 2010031860 A2 | | 3/2010 |
| WO | 2012102802 A1 | | 8/2012 |
| WO | WO 2012102802 A1 * | 8/2012 | .............. G02B 3/14 |
| WO | 2013127494 A1 | | 9/2013 |
| WO | WO 2013127494 A1 * | 9/2013 | .............. C02B 1/28 |

OTHER PUBLICATIONS

International Search Report for International Application No. PCT/EP2015/063830, mailed from the European Patent Office dated Feb. 2, 2016, 7 pages.
J.A. Barth et al., "Synthese und spektrale Charakterisierung von blauen Benzenazofarbstoffen Synthesis and Spectral Characterization of Blue Azo Dyes of the Benzene Series", Journal f. prakt. Chemie. Band 328, Heft 4, 1986, pp. 497-514. (as cited in the ISR).
Japanese Office Action dated Sep. 25, 2017 for Japanese Patent Application No. 2016-571194.
Chinese Office Action dated Apr. 4, 2018 for Chinese Application No. CN2015800333835.

* cited by examiner

CARRIER FLUID COMPOUNDS AND DYE COMPOUNDS FOR ELECTROWETTING APPARATUS

BACKGROUND

Display devices, for example electrowetting display devices, are known. Display elements of such a display device may each include a first fluid and a second fluid immiscible with the first fluid. A display effect providable by each display element is controllable in dependence on a configuration of the first and second fluids, which configuration is changeable using an applied voltage.

During manufacture of known display devices, it is necessary to provide a suitable and accurately dispensed volume of the first fluid in the display elements.

It is desirable to improve a method of providing the first fluid during manufacturing of an electrowetting apparatus.

DETAILED DESCRIPTION

Figure 1:
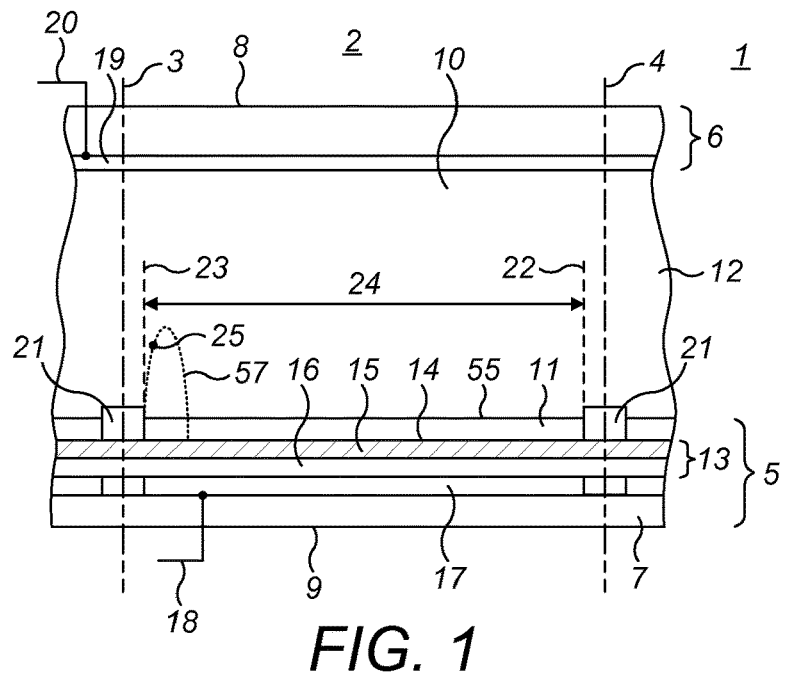
FIG. 1 shows schematically an example electrowetting display element.

Details of substituent groups and atoms which will be referred to herein are first described. These meanings apply unless explicitly stated to the contrary.

An alkyl group as referred to herein is a straight chain, branched or cyclic alkyl group. In examples, there are one or more carbon atoms in the alkyl group, for example in some examples having up to 30 carbon atoms, i.e. with 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms, for example having 1 to 4, 5 to 8, 9 to 12, 13 to 16, 17 to 20, 21 to 24, 25 to 30 carbon atoms, or any other sub-range within the range 1 to 30. In examples, a straight chain alkyl group may have 1 to 30 carbon atoms; in other examples, a branched chain alkyl group may have 3 to 30 carbon atoms; and in further examples a cyclic alkyl group may have 5 to 30 carbon atoms. In other examples the alkyl group has up to 22 carbon atoms, i.e. with 1, 2, 3, 4, 5, 6, 7, 8, 9, 10, 11, 12, 13, 14, 15, 16, 17, 18, 19, 20, 21 or 22 carbon atoms, for example having 1 to 4, 5 to 8, 9 to 12, 13 to 16, 17 to 20, 21 to 22 carbon atoms, or any other sub-range within the range 1 to 22. In examples, a straight chain alkyl group may have 1 to 22 carbon atoms; in other examples, a branched chain alkyl group may have 3 to 22 carbon atoms; and in further examples a cyclic alkyl group may have 5 to 22 carbon atoms. In a branched alkyl group described herein, there may be one, two or three branched carbon atoms. Further examples of alkyl groups are described later.

A haloalkyl group referred to herein is an alkyl group in accordance with the description of an alkyl group given in the paragraph above but with one, two or three of the hydrogen atoms replaced by a halogen atom, for example any of fluorine (F), chlorine (Cl), bromine (Br) and iodine (I); in some examples a halogen atom is bromine (Br). It is noted that a halogen atom referred to herein which is not part of a haloalkyl group is one of the halogen atoms listed here.

Any aryl group referred to herein is a monovalent aromatic hydrocarbon group having five, six or seven carbon atoms, for example any aromatic hydrocarbon having $C_5$ to $C_7$ carbon atoms, i.e. 5, 6 or 7 carbon atoms. Further, any such aryl group may be substituted on at least one aromatic carbon by for example, as defined herein, an alkyl group as defined herein, or another substituent as will be explained with reference to examples further below. The aryl group may have one, two, three, four or five substituent groups. Such an aryl group may for example be a phenyl group.

Any arylene group referred to herein is a divalent aromatic hydrocarbon group, with the divalent bonding sites being configured according to any of -ortho, -meta or -para sites for a six membered ring, at any of the 1 to 5 positions for a five membered ring, at any of the 1 to 6 positions for a six membered ring and at any of the 1 to 7 positions for a seven membered ring. Further, any such arylene group may for example be a single ring structure formed of five, six or seven carbon atoms which ring may be substituted on at least one aromatic carbon by an alkyl group as defined herein, or another substituent for example as will be explained with reference to examples further below. The arylene group may have one, two, three or four substituent groups.

Any alkoxy group referred to herein is an alkyl group in accordance with an alkyl group described herein, bonded to an oxygen, for example with the formula —O-alkyl.

A hydroxyl group referred to herein is the group —OH.

A heterocyclic group referred to herein includes saturated and unsaturated hydrocarbon groups with at least one heteroatom, for example nitrogen (N) or oxygen (O). For example, such an unsaturated group may be an aromatic hydrocarbon group with at least one heteroatom, for example nitrogen (N) or oxygen (O) conjugated in the aromatic system. The aromatic hydrocarbon group may form a five or six membered ring, including one, two or three heteroatoms, for example, and a number of carbon atoms to complete the ring, for example in the range $C_2$ to $C_5$, i.e. 2, 3, 4 or 5 carbon atoms. In other examples, such a saturated heterocyclic group may be a cyclic alkyl group referred to herein, with at least one of the carbon atoms of the cyclic alkyl group substituted with a heteroatom such as nitrogen (N) or oxygen (O). Such a saturated heterocyclic group may be a five or six membered ring, including one, two or three heteroatoms, for example, and a number of carbon atoms to complete the ring, for example in the range $C_2$ to $C_5$, i.e. 2, 3, 4 or 5 carbon atoms. Examples of such heterocyclic groups include a pyrrole group, a pyridine group, a furan group, a pyran group, a pyrrolidine group, a piperidine group, a tetrahydroofuran group, or an oxane group. The heterocyclic group may have one or more substituent groups bonded to the heterocycle group, for example at any of the 2, 3 and where appropriate 4 positions. Such substituent groups may be H or an alkyl group.

An amino group referred to herein includes any primary, secondary or tertiary amino, i.e. —$NH_2$ substituted respectively with zero, one or two alkyl or aryl groups as defined herein.

A nitro group referred to herein is the group —$NO_2$, i.e. including a nitrogen atom bonded to two oxygen atoms.

A cyano group referred to herein is the group —CN, i.e. a carbon atom bonded with a triple bond to a nitrogen. Such a group might alternatively be referred to as a nitrile group; i.e. a carbon with a triply bonded nitrogen substituent.

An amide group referred to herein is a group with a nitrogen bonded to a carboxy group, with the nitrogen being further substituted by two of a hydrogen atom, an alkyl group or an aryl group defined herein; i.e. for example having the formula —C(=O)N(AG)$_2$ where AG indicates an alkyl or aryl group defined herein.

A sulphonyl group referred to herein is a group with a sulphur atom bonded to two oxygen atoms via two double bonds. The sulphur atom is further bonded by a single bond to a hydrocarbon group such as an alkyl or an aryl group labelled AG and defined herein; i.e. —SO$_2$(AG).

A sulphonamide group referred to herein is a group with a sulphur atom bonded to two oxygen atoms via two double bonds and further bonded to a nitrogen atom which is bonded in turn either to two hydrogen atoms, to one alkyl or aryl group defined herein and to a hydrogen, or to two alkyl or aryl groups defined herein. Depending on the number of nitrogen substitutions, a sulphonamide group may have the formula: —S(=O)(=O)N(H)$_2$, —S(=O)(=O)N(H)(AG) or —S(=O)(=O)N(AG)$_2$ where AG is an alkyl or aryl group defined herein.

An amidophosphate group referred to herein is a group with a nitrogen bonded to a hydrogen atom and to a phosphorous atom. Such a group may also be referred to as a phosphoramidate. In such a group, the phosphorous atom is in turn bonded to one oxygen atom with a double bond and to the oxygen atom of each of two alkoxy groups defined herein. Such an amidophosphate group may therefore have the formula: —NH—P(=O)(—O-AG)$_2$ where AG is an alkyl or aryl group defined herein.

An ester group referred to herein is a group with a carbon atom doubly bonded to an oxygen atom and further singly bonded to an oxygen atom which in turn is bonded to an alkyl or an aryl group defined herein. Such an ester group may therefore have the formula —C(=O)—O-AG, i.e. COOAG, where AG is an alkyl or aryl group defined herein.

A thioalkyl group referred to herein includes any isomer of a thioalkyl group, i.e. an alkyl group, bonded to a sulphur, having the formula —S-alkyl where -alkyl is an alkyl group defined herein.

Examples will now be described.

FIG. 1 shows a diagrammatic cross-section of part of an example of an electrowetting display device 1, including a plurality of picture elements or display elements 2, one of which is shown in the Figure and which may also be referred to as an electrowetting cell or an electrowetting pixel. The lateral extent of the display element is indicated in the Figure by two dashed lines 3, 4. The display elements comprise a first support plate 5 and a second support plate 6. The support plates may be separate parts of each display element, but the support plates may be shared in common by the plurality of display elements. The support plates may include a glass or polymer substrate 6, 7 and may be rigid or flexible.

The display device has a viewing side 8 on which an image or display formed by the display device can be viewed and a rear side 9. In the Figure a surface of the first support plate 5, which surface is in this example a surface of the substrate 7, defines the rear side 9; a surface of the second support plate 6, which surface is in this example a surface of the substrate 6, defines the viewing side; alternatively, in other examples, a surface of the first support plate may define the viewing side. The display device may be of the reflective, transmissive or transflective type. The display device may be an active matrix driven display device. The plurality of display elements may be monochrome. For a colour display device the display elements may be divided in groups, each group having a different colour; alternatively, an individual display element may be able to show different colours.

A space 10 of each display element between the support plates is filled with two fluids: a first fluid 11 and a second fluid 12 at least one of which may be a liquid. The second fluid is immiscible with the first fluid. Therefore, the first fluid and the second fluid do not substantially mix with each other and in some examples do not mix with each other to any degree. The immiscibility of the first and second fluids is due to the properties of the first and second fluids, for example their chemical compositions; the first and second fluids tend to remain separated from each other, therefore tending not to mix together to form a homogeneous mixture of the first and second fluids. Due to this immiscibility, the first and second fluids meet each other at an interface labelled 55 in FIG. 1 for when no voltage is applied and labelled 57 for when a voltage is applied, which interface defines a boundary between the volume of the first fluid and the volume of the second fluid; this interface or boundary may be referred to as a meniscus. With the first and second fluids substantially not mixing with each other, it is envisaged in some examples that there may be some degree of mixing of the first and second fluids, but that this is considered negligible in that the majority of the volume of first fluid is not mixed with the majority of the volume of the second fluid.

The second fluid is electrically conductive or polar and may be water, or a salt solution such as a solution of potassium chloride in water. The second fluid may be transparent; it may instead be coloured, white, absorbing or reflecting. Details of the chemical composition of the first fluid, which is electrically non-conductive, are explained further below.

The first fluid may absorb at least a part of the optical spectrum. The first fluid may be transmissive for a part of the optical spectrum, forming a colour filter. For this purpose the first fluid may be coloured by addition of pigment particles or a dye. Alternatively, the first fluid may be black, i.e. absorb substantially all parts of the optical spectrum, or reflecting. A reflective first fluid may reflect the entire visible spectrum, making the layer appear white, or part of it, making it have a colour.

The support plate 5 includes an insulating layer 13. The insulating layer may be transparent or reflective. The insulating layer 13 may extend between walls of a display element. To avoid short circuits between the second fluid 12 and electrodes arranged under the insulating layer, layers of the insulating layer may extend uninterrupted over a plurality of display elements 2, as shown in the Figure. The insulating layer has a surface 14 facing the space 10 of the display element 2. In this example the surface 14 is hydrophobic. The thickness of the insulating layer may be less than 2 micrometers and may be less than 1 micrometer.

The insulating layer may be a hydrophobic layer; alternatively, it may include a hydrophobic layer 15 and a barrier layer 16 with predetermined dielectric properties, the hydrophobic layer 15 facing the space 10, as shown in the Figure. The hydrophobic layer is schematically illustrated in FIG. 1 and may be formed of Teflon® AF1600. The barrier layer 16 may have a thickness, taken in a direction perpendicular the plane of the substrate, between 50 nanometers and 500 nanometers and may be made of an inorganic material like silicon oxide or silicon nitride or a stack of these (for example, silicon oxide-silicon nitride-silicon oxide) or an organic material like polyimide or parylene.

The hydrophobic character of the surface 14 causes the first fluid 11 to adhere preferentially to the insulating layer 13, since the first fluid has a higher wettability with respect to the surface of the insulating layer 13 than the second fluid 12. Wettability relates to the relative affinity of a fluid for the surface of a solid. Wettability may be measured by the contact angle between the fluid and the surface of the solid. The contact angle is determined by the difference in surface tension between the fluid and the solid at the fluid-solid boundary. For example, a high difference in surface tension can indicate hydrophobic properties.

Each display element 2 includes a first electrode 17 as part of the support plate 5. In examples shown there is one such electrode 17 per element. The electrode 17 is electrically insulated from the first and second fluids by the insulating layer 13; electrodes of neighboring display elements are separated by a non-conducting layer. In some examples, further layers may be arranged between the insulating layer 13 and the electrode 17. The electrode 17 can be of any desired shape or form. The electrode 17 of a display element is supplied with voltage signals by a signal line 18, schematically indicated in the Figure.

The support plate 6 includes a second electrode 19, which may extend between walls of a display element or extend uninterruptedly over a plurality of display elements 2, as shown in the Figure. The electrode 19 is in electrical contact with the conductive second fluid 12 and is common to all display elements. The electrode may be made of for example the transparent conductive material indium tin oxide (ITO). A second signal line 20 is connected to the electrode 19. Alternatively, the electrode may be arranged at a border of the support plates, where it is in electrical contact with the second fluid. This electrode may be common to all elements, when they are fluidly interconnected by and share the second fluid, uninterrupted by walls. The display element 2 can be controlled by a voltage V applied between the signal lines 18 and 20. The signal line 18 can be coupled to a matrix of control lines on the substrate 7. The signal line 20 is coupled to a display driving system.

The first fluid 11 in this example is confined to one display element by walls 21 that follow the cross-section of the display element. The cross-section of a display element may have any shape; when the display elements are arranged in a matrix form, the cross-section is usually square or rectangular. Although the walls are shown as structures protruding from the insulating layer 13, they may instead be a surface layer of the support plate that repels the first fluid, such as a hydrophilic or less hydrophobic layer. The walls may extend from the first to the second support plate but may instead extend partly from the first support plate to the second support plate as shown in FIG. 1. The extent of the display element, indicated by the dashed lines 3 and 4, is defined by the center of the walls 21. The area of the surface 14 between the walls of a display element, indicated by the dashed lines 22 and 23, is called the display area 24, over which a display effect occurs. The display effect depends on an extent that the first and second fluids adjoin the surface defined by the display area, in dependence on the magnitude of the applied voltage V described above. The magnitude of the applied voltage V therefore determines the configuration of the first and second fluids within the electrowetting element. In other words, the display effect depends on the configuration of the first and second fluid in the display element, which configuration depends on the magnitude of the voltage applied to the electrodes of the display element. The display effect gives rise to a display state of the display element for an observer looking at the display device. When switching the electrowetting element from one fluid configuration to a different fluid configuration the extent of second fluid adjoining the display area surface may increase or decrease, with the extent of first fluid adjoining the display area surface decreasing or increasing, respectively.

Figure 2:
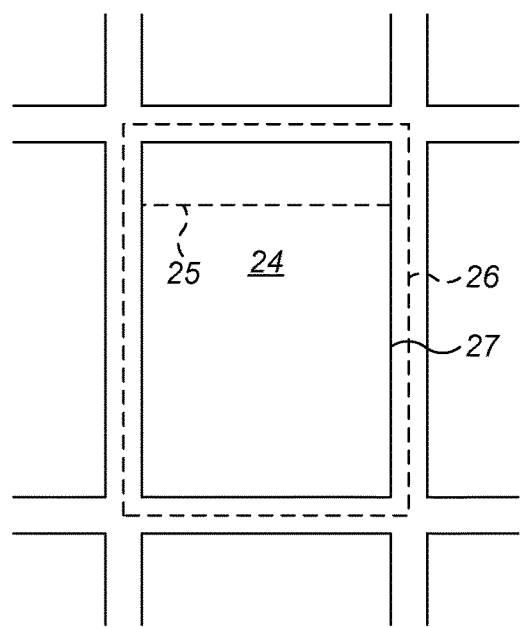
FIG. 2 shows a plan view of the example display element.

FIG. 2 shows a matrix of rectangular picture elements in a plan view of the hydrophobic surface 14 of the first support plate. The extent of the central picture element in FIG. 2, corresponding to the dashed lines 3 and 4 in FIG. 1, is indicated by the dashed line 26. Line 27 indicates the inner border of a wall; the line is also the edge of the display area 23.

When a zero or substantially zero voltage is applied between the electrodes 17 and 19, i.e. when the electrowetting element is in an off state, the first fluid 11 forms a layer between the walls 21, as shown in the FIG. 1. Application of a voltage will contract the first fluid, for example against a wall as shown by the dashed shape 25 in FIG. 1 or FIG. 2. The controllable shape of the first fluid, in dependence on the magnitude of applied voltage, is used to operate the picture element as a light valve, providing a display effect over the display area 23. For example, switching the fluids to increase adjoinment of the second fluid with the display area may increase the brightness of the display effect provided by the element.

This display effect determines the display state an observer will see when looking towards the viewing side of the display device. The display state can be from black to white with any intermediate grey state; in a colour display device, the display state may also include colour.

In known electrowetting display devices, the first fluid referred to above may comprise for example an alkane or silicone oil. It has now been observed that whilst such compounds exhibit many desirable properties for their use in an electrowetting display element, a lower vapour pressure would be desirable, for example to aid manufacture of the display elements.

Given the many numerous chemical compounds available, it is a complex and non-routine task to identify new compounds which offer suitable properties for the first fluid of an electrowetting display element. For example, properties of suitable compounds may include any of the following, though further properties are envisaged: suitable switching performance when a voltage is applied to change a configuration of the first and second fluids; a suitable viscosity, for example to aid the switching performance; suitable solvent properties, for example so the compound may function as a carrier fluid for a dye to be dissolved therein, so for example the first fluid provides reliable display effects in a variety of lighting conditions and temperature ranges; suitable safety properties, for example for manufacture and for the consumer; cost-effective; suitable immiscibility with the second fluid; and suitable optical transparency. Such properties apply to carrier fluid compounds and also where appropriate to dye compounds.

One property of such a first fluid compound, for example which functions as a carrier fluid, is a suitable vapour pressure. If the vapour pressure is too high, manufacturing a display element may be more complicated, given the volatility of the first fluid compound and its tendency to evaporate. This can for example lead to a reduced and/or inaccurately dispensed volume of the first fluid in the manufactured display elements and may also require more controlled and complex manufacturing techniques for handling the first fluid both safely and effectively to minimise evaporation.

New classes of chemical compounds for the first fluid in an electrowetting apparatus have now been identified. These compounds have a reduced vapour pressure compared with known first fluid compounds. Therefore a method of manufacturing an electrowetting apparatus may be simplified; further a volume of first fluid may be more accurately provided in a display element. Furthermore, it has been found that these new classes of compounds exhibit many other suitable properties required for them to perform suitably in an electrowetting display element, for example optical transparency and for example a suitable non-polar property for their function in an electrowetting display element. Indeed, these newly identified compounds offer properties which are at least comparable, but in some examples better overall, than known first fluid compounds.

For example, a viscosity of these newly identified compounds is sufficiently low to offer suitable performance in an electrowetting display element. It would be expected that to decrease a vapour pressure, a less volatile and therefore more viscous fluid would be required. However, the newly identified compound classes for electrowetting offer both a comparable viscosity with known first fluid compounds and moreover offer a reduced vapour pressure compared with such known compounds. Thus, the newly identified compounds for electrowetting offer an improved balance of vapour pressure and viscosity properties compared with known compounds.

In examples, the newly identified classes of compounds for electrowetting have a vapour pressure with a maximum value of 5 millimeters mercury (i.e. 5 mm Hg) when measured at a temperature of 20° Celsius. A dynamic viscosity of any such newly identified compound may be at most, i.e. less than or equal to, 37 centiPoise (cP) when measured at a temperature of 20° Celsius and in some examples greater than or equal to 0.5 cP; in some examples the dynamic viscosity of at least one of the compounds is in the range of: 0.5 to 37 cP, 0.5 to 35 cP, 0.5 to 30 cP, 0.5 to 25 cP, 0.5 to 20 cP, 0.5 to 15 cP, 0.5 to 10 cP, 0.5 to 9 cP, 0.5 to 8 cP, 0.5 to 7 cP. In other examples the dynamic viscosity in one of the following ranges may offer a particularly suitable viscosity for electrowetting performance: 0.5 to 6 cP, 0.5 to 5.5 cP, 0.5 to 5.0 cP, 0.5 to 4.5 cP, 0.5 to 4.0 cP, 0.5 to 3.5 cP, or 0.5 to 3.0 cP, when measured at a temperature of 20° Celsius. The dynamic viscosity values given herein are based on measurements taken with a Brookfield DVII+ pro viscosmeter for low viscosities with a CPE40 spindle (0.5° cone angle). Although specific values of dynamic viscosity and vapour pressure are given herein, it is to be appreciated that some variation from those values, within for example an accepted tolerance for error due to measuring techniques, is envisaged. Therefore, the term "about" may be used in association with any of the specified values.

In examples, the newly identified classes of compounds for the first fluid, for example which may act as a solvent, i.e. a carrier fluid, for at least one dye dissolved in the solvent, include any of:

a silane compound having the following general formula:

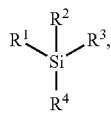

where Si is silicon; and
and a germane compound having the following general formula:

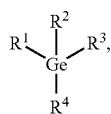

where Ge is germanium.

$R^1$, $R^2$, $R^3$ and $R^4$ are each an alkyl group Therefore, the compound including silicon may be referred to as a tetraalkylsilane and the compound including germanium may be referred to as a tetraalkylgermane.

Any alkyl group referred to herein for any of $R^1$, $R^2$, $R^3$ and $R^4$ includes any isomer of a straight chain or branched alkyl group. In examples, there are one or more carbon atoms in the alkyl group; for a branched alkyl group the minimum number of carbon atoms is 3, but may include a greater number of carbon atoms in accordance with the specific total number of carbon atom values listed below. For example, a total number of carbon atoms contained by any one of the alkyl groups $R^1$, $R^2$, $R^3$, $R^4$ may be at most, i.e. less than or equal to, 30; in other words this total number may be 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 carbon atoms and may for example be in one of the ranges of 1 to 4 carbon atoms, 5 to 8 carbon atoms, 9 to 12 carbon atoms, 13 to 16 carbon atoms, 17 to 20 carbon atoms, 21 to 24 carbon atoms, 25 to 28 carbon atoms, and 27 to 30 carbon atoms. Where any of the alkyl groups $R^1$, $R^2$, $R^3$ and $R^4$ is a branched alkyl group, a longest chain of carbon atoms in any one of the alkyl groups $R^1$, $R^2$, $R^3$ and $R^4$ is at most, i.e. less than or equal to, 24 carbon atoms long. Therefore, such a longest chain may be 3, 4, 5, 6, 7, 8, 9, 10, 11, 12, 13, 14, 15, 16, 17, 18, 19, 20, 21, 22, 23 or 24 carbon atoms long and may for example have 3 to 6 carbon atoms, 7 to 10 carbon atoms, 11 to 14 carbon atoms, 15 to 18 carbon atoms, 19 to 22 carbon atoms or 21 to 24 carbon atoms.

In examples, a total number of carbon atoms contained by all of the alkyl groups $R^1$, $R^2$, $R^3$ and $R^4$ when taken together, i.e. the total number is the sum of the number of carbon atoms of each of the alkyl groups $R^1$, $R^2$, $R^3$ and $R^4$, is at most, i.e. less than or equal to, 33 carbon atoms. Therefore, depending on the configuration of the alkyl groups this total number may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 carbon atoms, or may be in one of the ranges 1 to 4 carbon atoms, 5 to 8 carbon atoms, 9 to 12 carbon atoms, 13 to 16 carbon atoms, 17 to 20 carbon atoms, 21 to 24 carbon atoms, 25 to 28 carbon atoms, and 29 to 33 carbon atoms. This total may be considered as the total number of carbon atoms in one molecule of the solvent compound.

In examples, the alkyl group of each of $R^1$, $R^2$, $R^3$ and $R^4$ is a saturated alkyl group. In other words, each carbon-carbon bond in the alkyl group is a single bond, rather than a double or triple bond for example.

By controlling the configuration of the alkyl groups $R^1$, $R^2$, $R^3$ and $R^4$, for example in accordance with numbers of carbon atoms described above, the properties of a first fluid solvent compound may be tuned to provide an appropriate viscosity for example in combination for example with a desirable vapour pressure. Indeed, upper limits for the number of carbon atoms described above, for example the upper limit of 24 carbon atoms for the longest chain of carbon atoms in a branched alkyl group, are selected to provide suitable viscosity properties. A higher number of carbons than the specified upper limits may lead to viscosity properties for example which are not suitable for use in an electrowetting display element. Similarly, where any of the alkyl groups $R^1$, $R^2$, $R^3$ and $R^4$ are branched alkyl groups, the extent of branching is selected to provide suitable molecular properties, for example the viscosity. Each of $R^1$, $R^2$, $R^3$ and $R^4$ in examples may have the same branched alkyl group configuration or different ones of $R^1$, $R^2$, $R^3$ and $R^4$ may have different branching configurations compared with other ones of $R^1$, $R^2$, $R^3$ and $R^4$. Such branching may include secondary, tertiary and quaternary branching, where a carbon atom is bonded to two, three or four carbon atoms, respectively.

In some examples, the alkyl group of each of $R^1$, $R^2$, $R^3$ and $R^4$ is a straight chain, i.e. unbranched, alkyl group having the general formula —$(CH_2)_n CH_3$ where n is independently, for each of $R^1$, $R^2$, $R^3$ and $R^4$, in the range of 0 to 7. Therefore, the number of carbon atoms in a straight chain alkyl group of any of R', $R^2$, $R^3$ and $R^4$ may be 1, 2, 3, 4, 5, 6, 7 or 8 and may be in one of the ranges to 1 to 3 carbon atoms, 4 to 6 carbon atoms and 7 to 8 carbon atoms. The upper limit of n=7 carbon atoms (and therefore a total number of carbon atoms in one alkyl group of 8) applies where for example the number of carbon atoms contained by each of $R^1$, $R^2$, $R^3$ and $R^4$ is the same; thus, to keep to within the upper limit of 33 carbon atoms described above for the total number of carbon atoms of R1, R2, R3 and R4 when taken together, the maximum number of carbon atoms per alkyl group is 8 (i.e. 32 divided by 4), and the compound may therefore have the formula Si—$((CH_2)_7 CH_3)_4$ or Ge—$((CH_2)_7 CH_3)_4$.

Examples of such a compound of the first fluid will be now be described, where each of $R^1$, $R^2$, $R^3$ and $R^4$ contains the same number of carbon atoms. In examples, each of $R^1$, $R^2$, $R^3$ and $R^4$ is independently a straight chain alkyl group; in other examples each of $R^1$, $R^2$, $R^3$ and $R^4$ is independently a branched alkyl group.

Example 1

In this example the compound has the following formula:

where n=1 for each of $R^1$, $R^2$, R3 and R4 and the compound may be referred to as tetraethylsilane (TES). The compound has a vapour pressure of 4.4 mmHg when measured at 20° Celsius and a dynamic viscosity of 0.68 cP when measured at 20° Celsius. The compound may be obtained from Gelest, Inc., 11 East Steel Road, Morrisville, Pa. 19067, USA, under product code SIT7115.0 or Tokyo Chemical, Inc., 4-10-2 Nihonbashi-honcho, Chuo-ku, Tokyo 103-0023, Japan, under product code T1552.

Example 2

In this example the compound has the following formula:

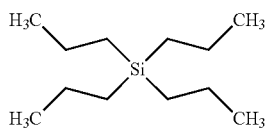

where n=2 for each of $R^1$, $R^2$, $R^3$ and $R^4$ and the compound may be referred to as tetrapropylsilane (TPS). The compound has a dynamic viscosity of 1.34 cP when measured at 20° Celsius. The compound may be synthesised for example as follows:

To a mixture of 100.0 grams (g) magnesium (4.17 moles (mol)) and 200 milliliters (mL) tetrahydrofuran (THF) there was added 5 g 1-bromopropane. The mixture was cooled with a cold-water bath after Grignard agent formation had started. 450 mL THF was added, followed by the slow addition of 1-bromopropane (total amount 500 g, 4.065 mol) at temperatures between 20° Celsius (° C.) and 75° C. over a period of 2½ hours. An additional 200 mL THF was added and the mixture was heated for 4 hours (h) at 60° C., then it was cooled in ice. Silicon tetrachloride (108.42 g, 0.638 mol) was added over a 2½ h period at 15-38° C. During this addition, another 250 mL THF was added in order to maintain a well-stirrable suspension. The mixture was heated for 1 h at 60° C., stirred overnight, then heated for 8 h at 65° C., and for 4 h at 75° C. Water (50 mL) and 6 normality (N) hydrochloric acid (100 mL) were added very slowly to the suspension at ca. 60° C. The mixture was further diluted with 6N hydrochloric acid (500 mL) and stirred mechanically for 3 h before the liquid was decanted and partially concentrated on a rotary evaporator (i.e. a rotavap). The residue was treated with 300 mL tertiary-butyl methyl ether (TBME), washed with water and concentrated on the rotavap. After extraction with pentane and heptane the combined organic layers were eluted over a silica column with heptane. Rotary evaporation and Kugelrohr distillation yielded 114.9 g of the product (0.573 mol, 90% yield).

Example 3

In this example the compound has the following formula:

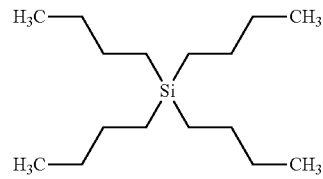

where n=3 for each of $R^1$, $R^2$, $R^3$ and $R^4$ and the compound may be referred to as tetrabutylsilane (TBS). The compound has a dynamic viscosity of 3.69 cP when measured at 20° Celsius. The compound may be synthesised for example as follows:

A mixture of chlorotributylsilane (25.0 g, 0.106 mol) and 75 mL heptane was cooled with an ice-bath. n-Butyllithium in hexanes (70 mL 2.5 N, 0.175 mol) was added over a 20 minute period. The cooling bath was removed and the mixture was stirred overnight, then heated for 6 h at 60° C. The mixture was cooled with ice and 75 mL THF was added in portions, resulting in a temperature rise to 35° C. The mixture was stirred for 5 days, then 100 mL water was added. The layers were separated, the lower layer was extracted with some heptane and the organic layers were dried over sodium sulfate, then rotary evaporated. The residue was chromatographed on 80 g silica, elution being performed with heptane. Rotary evaporation of the eluate and Kugelrohr distillation of the residue yielded 25.60 g of the product (99.8 mmol, 94% yield).

Example 4

In this example the compound has the following formula:

where n=1 for each of $R^1$, $R^2$, $R^3$ and $R^4$. The compound may be referred to as tetraethylgermane (TEG). The compound has a dynamic viscosity of 0.66 cP when measured at 20° Celsius. The compound may be obtained from Gelest, Inc. under product code no. GET7150 or Tokyo Chemical, Inc. under product code no. T1157.

In further examples, the number of carbon atoms contained by any one, for example one or more, of $R^1$, $R^2$, $R^3$ and $R^4$ is different from a number of carbon atoms contained by a different one of $R^1$, $R^2$, $R^3$ and $R^4$. One example is now described.

Example 5

In this example the compound has the following formula:

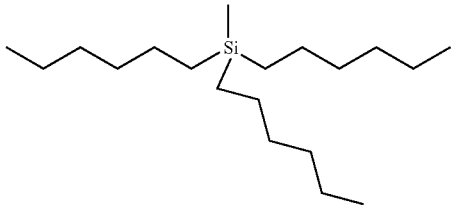

where n=5 for each of $R^1$ and $R^4$, n=0 for $R^2$ and n=4 for $R^3$. The compound may be referred to as trihexylmethylsilane (THMS). The compound has a dynamic viscosity of 5.32 cP when measured at 20° Celsius. The compound may be obtained from Gelest, Inc. under product code no. SIM6559.0. The silane and germane compounds described herein for the first fluid, for examples those of examples 1 to 5, are found to function as a suitable carrier fluid for use in an electrowetting display element. Therefore, such a compound may act as a suitable solvent for dissolving a dye compound used in an electrowetting display element, to form an electrowetting ink for example, or may provide a suitable medium for suspending pigment particles therein. Further details of such dye compounds will be described in further detail below. Suitable pigments may include for example carbon black, a phthalocyanine pigment, an azo pigment or a diketopyrrolopyrrole (DPP) pigment.

Examples of dye compounds will now be described. These dye compounds are newly identified as being usable in an electrowetting apparatus, for example in a first fluid described above, and have at least one desirable property for functioning in an electrowetting apparatus, for example the properties previously described. Any such dye compound is at least partly dissolvable in any of the examples of carrier fluid compounds described previously, for example the silane and germane compounds described above. Thus, a fluid including such a dye compound at least partly dissolved in such a carrier fluid provides an effective first fluid for electrowetting apparatus. In other examples any such dye compound is at least partly dissolvable in other known carrier fluids for the first fluid, for example silicone oil or an alkane such as decane.

In examples, of a fluid for an electrowetting apparatus, such as that described above, the fluid includes at least one azo dye compound having the following formula:

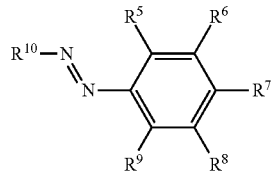

(Formula 1)

where $R^5$ is H; $R^6$ is an alkoxy group having the formula —O—$R^a$, where $R^a$ is an alkyl group; $R^7$ is selected from: an amino group having the formula —N($R^b$)($R^c$), with each of $R^b$ and $R^c$ being an alkyl group, or —N=N—$Het^1$ where $Het^1$ is a heterocyclic group; $R^8$ is H; $R^9$ is selected from: an alkoxy group having the formula —O—$R^d$, where $R^d$ is an alkyl group; an amide group having the formula —NH—C(=O)$R^e$, where $R^e$ is an alkyl group; a sulphonamide group having the formula —NH—S(=O)(=O)—$R^f$, where $R^f$ is an alkyl group, or an amidophosphate group having the formula —NH—P(=O)(—O—$R^g$)$_2$, where $R^g$ is independently an alkyl group (each $R^g$ alkyl group of the amidophosphate group may be the same or different), $R^{10}$ has the formula B-A-, where B has the formula:

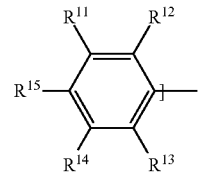

where $R^{11}$ is H; $R^{12}$ is selected from: H, a cyano group having the formula —CN, an alkoxy group having the formula —O—$R^h$, where $R^h$ is an alkyl group, an alkyl group $R^i$ for example a methyl alkyl group, or a halogen atom; $R^{13}$ is selected from:

H, a cyano group having the formula —CN, an alkyl group $R^j$ for example a methyl alkyl group, or a halogen atom; $R^{14}$ is selected from: H, a cyano group having the formula —CN, a nitro group having the formula —NO$_2$, or an alkoxy group having the formula —O—$R^k$, where $R^k$ is an alkyl group; $R^{15}$ is selected from: a cyano group having the formula —CN, a nitro group having the formula —NO$_2$, an ester group having the formula —COO—$R^l$, where $R^l$ is an alkyl group, an alkoxy group having the formula —O—$R^m$, where $R^m$ is an alkyl group, an alkyl group $R^n$, a halogen atom, or a sulphonyl group having the formula —SOOOH;

where A is selected from: a single bond, the formula:

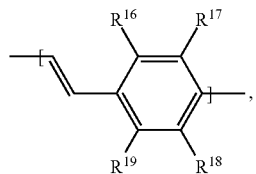

or
the formula:

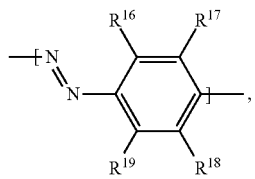

where $R^{16}$ is H; $R^{17}$ is selected from: H, or an alkoxy group having the formula —O—$R^o$, where $R^o$ is an alkyl group; $R^{18}$ is H; $R^{19}$ is selected from: H, or an alkoxy group having the formula —O—$R^p$, where $R^p$ is an alkyl group. Thus in some examples the dye compound may be a bisazo dye compound.

In examples, the alkyl group of one or more of: $R^a$, $R^b$, $R^c$, $R^d$, $R^e$, $R^f$, $R^g$, $R^h$, $R^i$, $R^j$, $R^k$, $R^l$, $R^m$, $R^n$, $R^o$, $R^p$ is independently selected from: a straight chain alkyl group having 1 to 22 carbon atoms, a branched alkyl group having 3 to 22 carbon atoms, or a cyclic alkyl group having 5 to 22 carbon atoms.

In examples described above and below where an alkyl group of a dye compound has a number of carbon atoms in the range of 1 to 22, it has been found that more than 22 carbon atoms can increase a viscosity of a dye compound to the extent that it degrades its performance within an electrowetting apparatus. Such alkyl groups may in some examples instead be a haloalkyl group which includes a bromide atom.

In some examples an alkyl group having the formula:

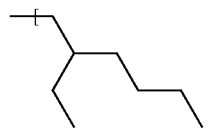

is described herein; such an alkyl group offers suitable solubility properties of the dye compound in a carrier fluid such as a silane or germane carrier fluid described in examples herein.

Further, or in further examples where the dye compound is according to Formula 1, $R^a$ is selected from:
a branched alkyl group having 3 to 22 carbon atoms,
a branched alkyl group having 3 to 8 carbon atoms,
a branched alkyl group having 8 carbon atoms, or
a branched alkyl group such that $R^6$ has the formula:

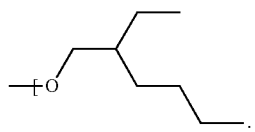

Further, or in further examples where the dye compound is according to Formula 1, $R^7$ is the amino group having the formula —N($R^b$)($R^c$), the alkyl group of $R^b$ and $R^c$ are each independently selected from:
a straight chain alkyl group having 1 to 22 carbon atoms,
a straight chain alkyl group having 1 to 8 carbon atoms,
a straight chain alkyl group having 8 carbon atoms,
a straight chain alkyl group having 6 carbon atoms,
a straight chain alkyl group having 1 to 5 carbon atoms,
a straight chain alkyl group having 5 carbon atoms,
a branched alkyl group having 3 to 22 carbon atoms,
a branched alkyl group having 3 to 8 carbon atoms,
a branched alkyl group having 8 carbon atoms,
a branched alkyl group such that the amino group of $R^7$ has the formula:

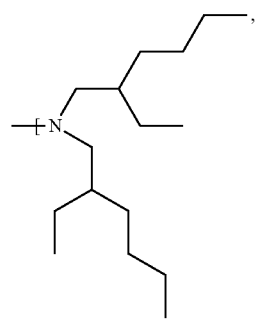 [SMILES: CCCCC(CC)CN(C)CC(CC)CCCC]

a straight chain alkyl group having 5 carbon atoms, or
a straight chain alkyl group having 4 carbon atoms.

In such examples, it is noted that a tertiary amino provides suitable solubility in a carrier fluid, for example the silane or germane examples described above. Primary and secondary aminos are less soluble in such carrier fluids and are therefore less suitable for use in an electrowetting apparatus.

Further, or in further examples where the dye compound is according to Formula 1, $R^7$ is —N=N—$Het^1$ where $Het^1$ is a heterocyclic group selected from: a five membered heterocyclic ring, a six membered heterocyclic ring, a five membered heterocyclic aromatic ring containing 1 to 3 heteroatoms, a six membered heterocyclic aromatic ring containing 1 to 3 heteroatoms, a five membered heterocyclic aromatic ring containing 1 heteroatom which is an N atom, a six membered heterocyclic aromatic ring containing 1 heteroatom which is an N atom, a five membered heterocyclic aromatic ring containing 1 heteroatom which is an N atom, where the —N=N— group is bonded to the heterocyclic aromatic ring at the 2 position relative to the heteroatom (as will be appreciated by the skilled person), a six membered heterocyclic aromatic ring containing 1 heteroatom which is an N atom, where the —N=N— group is bonded to the heterocyclic aromatic ring at the 2 position, a five membered heterocyclic aromatic ring containing 1 heteroatom substituted with an alkyl group selected from: an alkyl group having 1 to 22 carbon atoms, a straight chain alkyl group having 1 to 22 carbon atoms, a straight chain alkyl group having 1 to 8 carbon atoms, a straight chain alkyl group having 8 carbon atoms, a branched alkyl group having 3 to 22 carbon atoms, a branched alkyl group having 3 to 8 carbon atoms, a branched alkyl group having 8 carbon atoms, or a branched alkyl group having the formula:

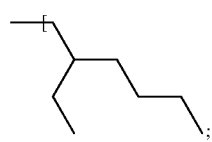

a six membered heterocyclic aromatic ring containing 1 heteroatom substituted with an alkyl group selected from: an alkyl group having 1 to 22 carbon atoms, a straight chain alkyl group having 1 to 22 carbon atoms, a straight chain alkyl group having 1 to 8 carbon atoms, a straight chain alkyl group having 8 carbon atoms, a branched alkyl group having 3 to 22 carbon atoms, a branched alkyl group having 3 to 8 carbon atoms, a branched alkyl group having 8 carbon atoms, or a branched alkyl group having the formula:

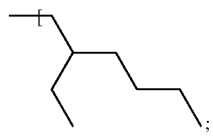

or a five membered heterocyclic aromatic ring having the formula:

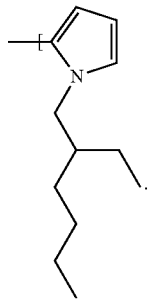

Further, or in further examples where the dye compound is according to Formula 1, one or more of the following apply: the alkyl group of $R^d$ is selected from: a branched alkyl group having 3 to 22 carbon atoms, a branched alkyl group having 3 to 8 carbon atoms, a branched alkyl group having 8 carbon atoms, or a branched alkyl group such that the alkoxy group of $R^9$ has the formula:

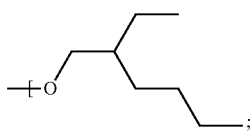

or the alkyl group of $R^e$ is selected from: a branched alkyl group having 3 to 22 carbon atoms, a branched alkyl group having 3 to 7 carbon atoms, a branched alkyl group having 7 carbon atoms, or a branched alkyl group such that the amide group of $R^9$ has the formula:

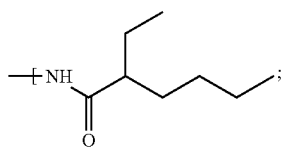

or the alkyl group of $R^f$ is selected from: a branched alkyl group having 3 to 22 carbon atoms, a branched alkyl group having 3 to 8 carbon atoms, a branched alkyl group having 8 carbon atoms, or a branched alkyl group having the formula:

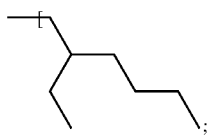

or the alkyl group of $R^g$ is selected from: a straight chain alkyl group having 1 to 22 carbon atoms, a straight chain alkyl group having 2 carbon atoms, a branched alkyl group having 3 to 22 carbon atoms, a branched alkyl group having 3 to 8 carbon atoms, a branched alkyl group having 8 carbon atoms, or a branched alkyl group having the formula:

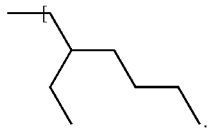

Further, or in further examples with the dye compound according to Formula 1, B has a formula selected from:
a formula where $R^{12}$ is a cyano group having the formula —CN, $R^{13}$ is H, $R^{14}$ is H and $R^{15}$ is a cyano group having the formula —CN, a formula where $R^{12}$ is H, $R^{13}$ is H, $R^{14}$ is H and $R^{15}$ is a cyano group having the formula —CN,
a formula where: $R^{12}$ is an alkoxy group having the formula —O—$R^h$ where $R^h$ is an alkyl group selected from: a branched alkyl group having 3 to 22 carbon atoms, a branched alkyl group having 3 to 8 carbon atoms, a branched alkyl group having 8 carbon atoms, or a branched alkyl group having the formula:

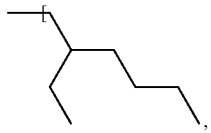

$R^{13}$ is H, $R^{14}$ is an alkoxy group having the formula —O—$R^k$ where $R^k$ is an alkyl group selected from: a branched alkyl group having 3 to 22 carbon atoms, a branched alkyl group having 3 to 8 carbon atoms, a branched alkyl group having 8 carbon atoms, or a branched alkyl group having the formula:

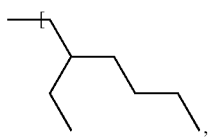

$R^{15}$ is a nitro group having the formula —$NO_2$.
Further, or in further examples with the dye compound according to Formula 1, A is selected from: a single bond, or where A has the formula:

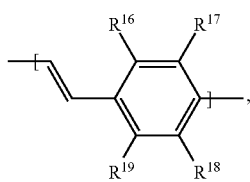

or the formula:

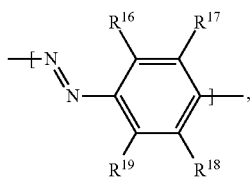

$R^o$ and $R^p$ are independently selected from: a branched alkyl group having 3 to 22 carbon atoms, a branched alkyl group having 3 to 8 carbon atoms, a branched alkyl group having 8 carbon atoms, or a branched alkyl group having the formula:

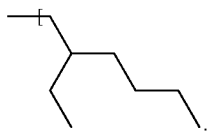

In an example of a dye compound according to Formula 1, the dye compound has the following formula:

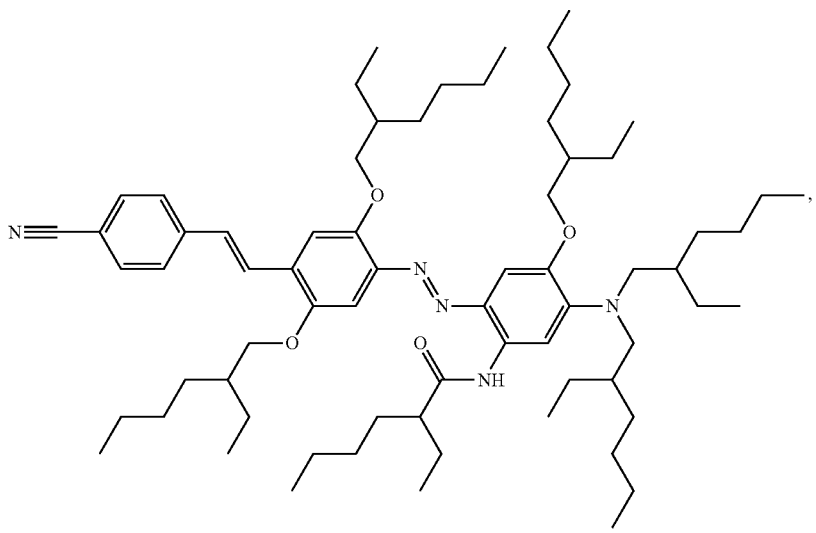 [SMILES: CCCCC(CC)COc1cc(/N=N/c2cc(OCC(CC)CCCC)c(N(CC(CC)CCCC)CC(CC)CCCC)cc2NC(=O)C(CC)CCCC)c(OCC(CC)CCCC)cc1/C=C/c1ccc(C#N)cc1]

This compound N-(5-(bis(2-ethylhexyl)amino)-2-((E)-(4-((E)-4-cyanostyryl)-2,5-bis((2-ethylhexyl)oxy)phenyl)diazenyl)-4-((2-ethylhexyl)oxy)phenyl)-2-ethylhexanamide may be synthesised as follows:

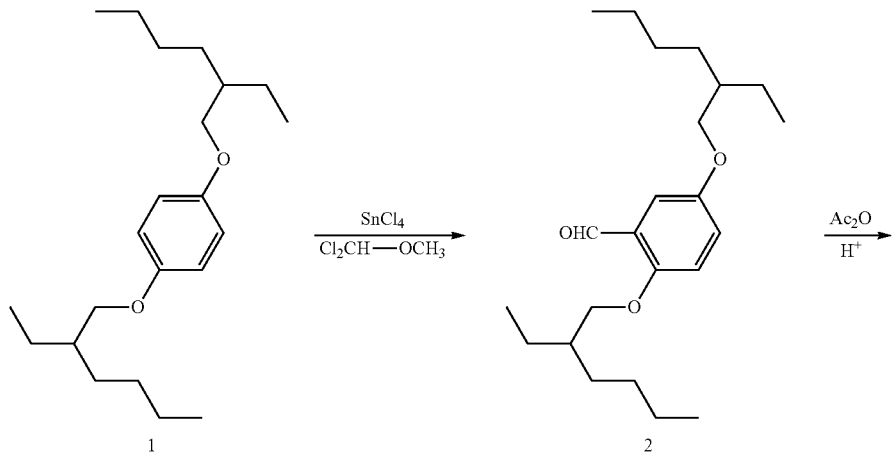

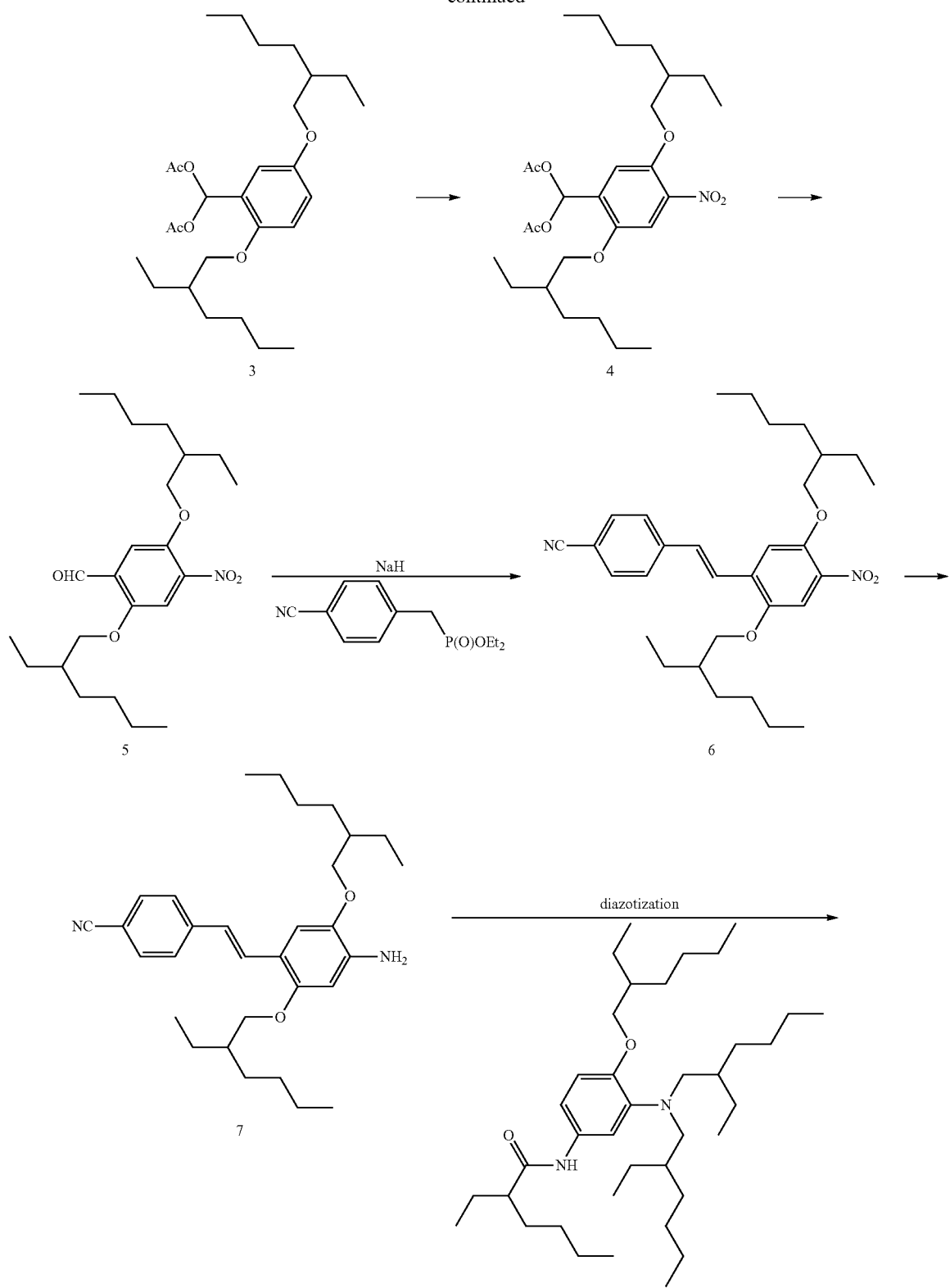

-continued

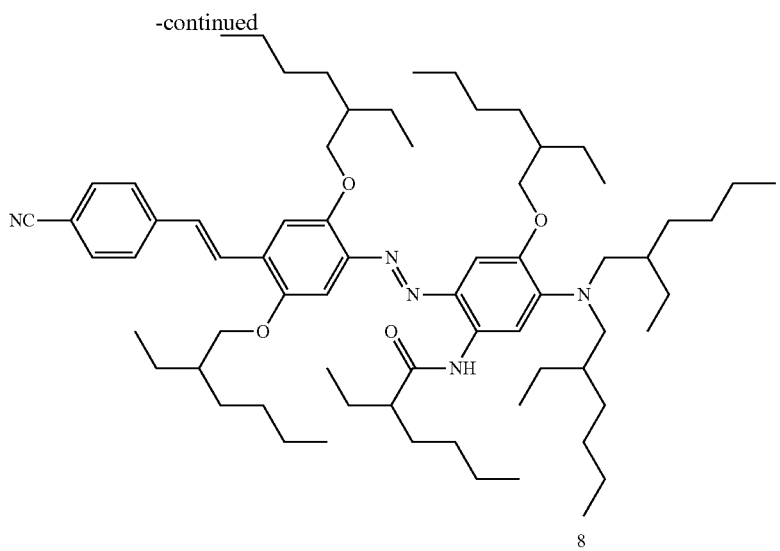

8

1,4-bis((2-ethylhexyl)oxy)benzene

A mixture of hydroquinone (22.0 g, 0.20 mol), 2-ethylhexyl bromide (90.0 g, 0.466 mol), potassium carbonate (60.0 g, 0.434 mol), 1.0 g tetrabutylammonium bromide and 100 mL 2-butanone was heated under reflux for 24 h. The mixture was rotary evaporated and the residue was stirred with 250 mL heptane, then filtered. The same procedure was repeated. The filtrates were rotary evaporated and the residue was purified by Kugelrohr distillation to give 49.25 g of 1,4-bis((2-ethylhexyl)oxy)benzene (0.147 mol, 74%).

2,5-bis((2-ethylhexyl)oxy)benzaldehyde

A mixture of 1,4-bis((2-ethylhexyl)oxy)benzene (32.08 g, 96.0 mmol) and dichloromethyl methyl ether (13.10 g, 0.114 mol) in 50 mL dichloromethane was added over a 75 min period to an ice-cooled solution of tin(IV)chloride (27.1 g, 0.104 mol) in 45 mL dichloromethane at 3-6° C. The mixture was stirred for 2 h in the ice-bath, then poured into 60 mL cold 6 N hydrochloric acid. The layers were separated and the aqueous layer was extracted with 100 mL dichloromethane. The organic layers were stirred for 20 min with ca. 20 mL some sodium carbonate in water, the layers were separated, the organic layer was dried and rotary evaporated to give 2,5-bis((2-ethylhexyl)oxy)benzaldehyde, which was used as such in the next step.

(2,5-bis((2-ethylhexyl)oxy)phenyl)methylene Diacetate 2,5-Bis((2-ethylhexyl)oxy)benzaldehyde was dissolved in 70 mL acetic anhydride, the mixture was cooled in ice and 4 drops of 96% sulphuric acid were added (giving a temperature rise to 14° C.). The mixture was stirred for 3 h, allowing the temperature to rise to 16° C. Sodium bicarbonate (5 g) was added, the mixture was stirred for 5 min, 100 g ice was added, as well as 100 mL heptane. The mixture was stirred for 10 min, then the layers were separated (there was a small intermediate layer). The two lower layers were extracted with 75 mL heptane. The heptane layers were dried and rotary evaporated, then put under high vacuum at 60° C. to yield ca. 40 g of (2,5-bis((2-ethylhexyl)oxy)phenyl)methylene diacetate, which was used as such in the next step.

(2,5-bis((2-ethylhexyl)oxy)-4-nitrophenyl)methylene Diacetate

A solution of (2,5-bis((2-ethylhexyl)oxy)phenyl)methylene diacetate in 100 mL acetic anhydride was cooled in ice. Nitric acid (90%; 12.10 g, 0.173 mol) was added over a 1 h period at 4-10° C. The mixture was stirred for 1 h, allowing the temperature to rise to 10° C. 50 g ice was added, as well as a suspension of 16 g sodium bicarbonate in 50 ml, water (addition in portions) and 100 mL heptane. The mixture was stirred for 30 min, some more ice being added in order to keep the temperature below 30° C. The layers were separated and the aqueous layer was extracted with 2×100 mL heptane containing some toluene. The combined organic layers were stirred with 50 mL ice-water/5 g sodium bicarbonate, the layers were separated, the organic layer was dried and rotary evaporated to give 45.34 g (89.07 mmol, 93% yield) of (2,5-bis((2-ethylhexyl)oxy)-4-nitrophenyl)methylene diacetate, which was used as such in the next step.

2,5-bis((2-ethylhexyl)oxy)-4-nitrobenzaldehyde (2,5-bis((2-ethylhexyl)oxy)-4-nitrophenyl)methylene diacetate (29.64 g, 58.23 mmol) was dissolved in 125 mL ethanol. A mixture of 6.6 g 96% sulphuric acid and 15 mL water was added and the mixture was heated for 4 h at 70° C. Most of the ethanol was removed by rotary evaporation. 20 mL water was added and extraction was performed with 2×150 mL TBME. The successive organic layers were washed with 30 mL water, then dried and rotary evaporated to yield 2,5-bis((2-ethylhexyl)oxy)-4-nitrobenzaldehyde (21.54 g, 52.92 mmol, 91% yield) which was used as such in the next step.

Diethyl 4-cyanobenzylphosphonate

A mixture of 4-(chloromethyl)benzonitrile (9.10 g, 60.0 mmol), triethyl phosphite (35.0 g, 0.211 mol) and 10 mL toluene was heated for 18 h at 135° C. The mixture was rotary evaporated and then heated under high vacuum to remove the last triethyl phosphite. The residue, weighing 15.62 g, was used as such.

(E)-4-(2,5-bis((2-ethylhexyl)oxy)-4-nitrostyryl)benzonitrile

A solution of diethyl 4-cyanobenzylphosphonate (15.62 g, 65.84 mmol theor.), 2,5-bis((2-ethylhexyl)oxy)-4-nitrobenzaldehyde (21.54 g, 52.92 mmol theor.) in 150 mL THF was cooled in ice. Potassium t-butoxide (8.49 g, 75.8 mmol) in 100 mL THF was added in ca. 30 min. The mixture was stirred overnight and rotary evaporated at 55° C. 100 mL water was added to the residue and extraction was performed with 2×200 mL toluene. Washing with 25 mL water, drying and rotary evaporation yielded a residue which was purified by chromatography on 140 g silica. Elution with heptane, containing increasing amounts of toluene, yielded (E)-4-(2,5-bis((2-ethylhexyl)oxy)-4-nitrostyryl)benzonitrile (17.55 g, 34.68 mmol, 66% yield) as a yellow solidifying oil.

(E)-4-(4-amino-2,5-bis((2-ethylhexyl)oxy)styryl)benzonitrile (E)-4-(2,5-bis((2-ethylhexyl)oxy)-4-nitrostyryl)benzonitrile (17.55 g, 34.68 mmol) was mixed with 250 mL ethanol and tin(II)chloride dehydrate (40.0 g, 177.3 mmol). The mixture was gradually warmed to 70° C., and kept at that temperature for 1 h. Rotary evaporation was followed by addition of 200 mL water and 200 mL TBME. An excess of sodium bicarbonate was added slowly to the well-stirred mixture. The mixture was allowed to stand for 2 days, then the layers were separated and the aqueous layer (a suspension) was extracted with 2×200 mL TBME. Drying and rotary evaporation left a residue which was chromatographed on 117 g silica. Elution with heptane, containing increasing amounts of toluene and ethyl acetate yielded (E)-4-(4-amino-2,5-bis((2-ethylhexyl)oxy)styryl)benzonitrile (9.32 g, 19.58 mmol, 56% yield) as a pale-yellow oil.

N-(5-(bis(2-ethylhexyl)amino)-2-((E)-(4-((E)-4-cyanostyryl)-2,5-bis((2-ethylhexyl)oxy)phenyl)diazenyl)-4-((2-ethylhexyl)oxy)phenyl)-2-ethylhexanamide (E)-4-(4-amino-2,5-bis((2-ethylhexyl)oxy)styryl)benzonitrile (4.62 g, 9.71 mmol) was dissolved in 100 mL acetic acid and 20 mL propionic acid. The solution was cooled in ice and nitrosylsulfuric acid (40% solution in sulphuric acid; 3.12 g, 9.83 mmol) was added slowly. After addition of some of the nitrosylsulfuric acid a thick precipitate formed and the temperature rose to 8° C. 25 mL dioxane was added after some time, resulting in a solution and in a temperature drop to 2° C. The remainder of the nitrosylsulfuric acid was added at 2-4° C. in about 10 minutes. The dark red-brown solution was stirred for 20 min, then a solution of the trialkylated amide 9 (7.80 g, 13.28 mmol; obtained in 3 steps from 2-nitro-4-aminophenol via acylation, hydrogenation and alkylation) in 25 mL dioxane was added over a 10 min period at 2-5° C. The mixture was stirred for 30 min, allowing the temperature to rise to 10° C. The mixture was cooled with ice and 15 mL 30% sodium hydroxide solution was added over a 30 min period at 5-8° C. The mixture was stirred for 16 h and then poured into 150 mL toluene/100 mL water. The layers were separated, the aqueous layer was extracted with 2×150 mL toluene and the successive organic layers were washed with 50 mL water. Drying and rotary evaporation yielded a residue which was purified by chromatography.

In another example of a dye compound according to Formula 1, the dye compound has the following formula:

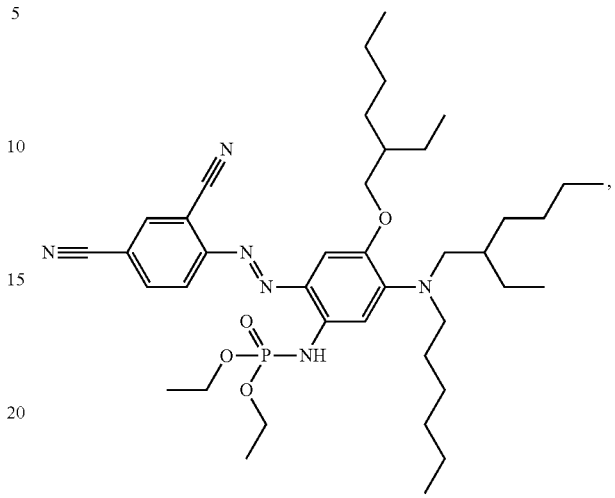

This compound (E)-diethyl(2-((2,4-dicyanophenyl)diazenyl)-5-((2-ethylhexyl)(hexyl)amino)-4-((2-ethylhexyl)oxy)phenyl)phosphoramidate may be synthesised as follows:

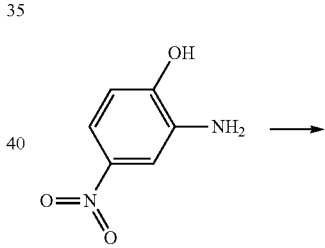

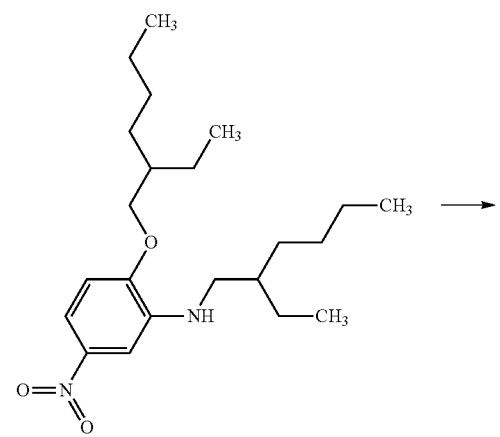

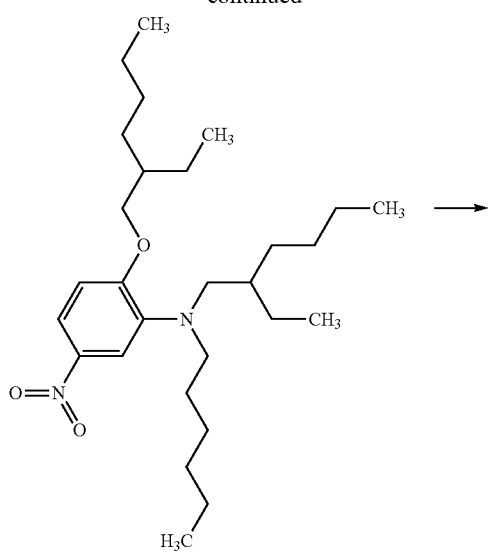

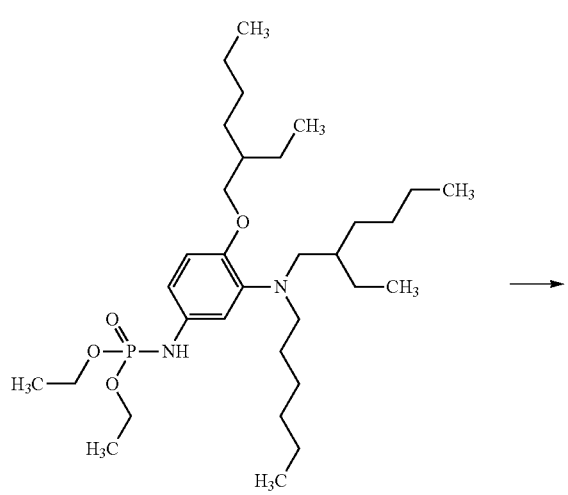

N-(2-ethylhexyl)-2-((2-ethylhexyl)oxy)-5-nitroaniline

A mixture of 2-amino-4-nitrophenol (3.09 g, 20.0 mmol), 2-ethylhexyl bromide (20.3 g, 0.105 mol) and N,N-diisopropylethylamine (13.0 g, 0.101 mol) was heated for 7 h at 134° C. The mixture was cooled and worked up with water and heptane. Drying, rotary evaporation and purification by column chromatography over silica gave the N,O-dialkylated compound N-(2-ethylhexyl)-2-((2-ethylhexyl)oxy)-5-nitroaniline.

N-(2-ethylhexyl)-2-((2-ethylhexyl)oxy)-N-hexyl-5-nitroaniline

N-(2-ethylhexyl)-2-((2-ethylhexyl)oxy)-5-nitroaniline (25 g) was heated for 7 d at 140° C. with 1-bromohexane (40 mL, 0.284 mol), sodium carbonate (15.95 g, 0.150 mol) and 0.40 g tetrabutylammonium bromide. The mixture was cooled and 50 mL water was added. The mixture was extracted with 2×50 mL toluene. Drying and rotary evaporation gave a residue which was chromatographed on 100 g silica. Elution with heptane yielded the product N-(2-ethylhexyl)-2-((2-ethylhexyl)oxy)-N-hexyl-5-nitroaniline (9.35 g).

$N^1$-(2-ethylhexyl)-6-((2-ethylhexyl)oxy)-$N^1$-hexyl-benzene-1,3-diamine

Hydrogenation of 18.70 g of N-(2-ethylhexyl)-2-((2-ethylhexyl)oxy)-N-hexyl-5-nitroaniline in a mixture of 250 mL THF and 20 mL acetic acid using 10% Pd/C as catalyst gave, after filtration, rotary evaporation and heating at 80° C. under high vacuum, a residue, which was heated under reflux for 20 h with 10.0 g potassium hydroxide in 100 mL ethanol. Rotary evaporation, addition of 75 mL water, extraction with 2×100 mL TBME, washing of the successive organic layers with 25 mL water, drying and rotary evaporation gave 8.67 g of $N^1$-(2-ethylhexyl)-6-((2-ethylhexyl)oxy)-$N^1$-hexylbenzene-1,3-diamine.

Diethyl(3-((2-ethylhexyl)(hexyl)amino)-4-((2-ethylhexyl)oxy)phenyl)phosphoramidate To an ice-cooled mixture of 8.67 g $N^1$-(2-ethylhexyl)-6-((2-ethylhexyl)oxy)-$N^1$-hexylbenzene-1,3-diamine (20.03 mmol), 75 mL toluene and N,N-diisopropylethylamine (12.95 g, 0.100 mol) was added diethyl chlorophosphate (7.35 g, 42.60 mmol) over a 20 min period. The mixture was stirred for 3 d (days) at room temperature (RT), then warmed for 5 h at 80° C., before being cooled to RT. After addition of 50 mL of water and 10.0 g of sodium bicarbonate, the mixture was stirred for 30 min and the layers were separated and extracted with 100 mL toluene. Drying and rotary evaporation yielded a residue which was chromatographed over 70 g silica, elution being done with heptane containing increasing amounts of ethyl acetate yielding 4.40 g of diethyl(3-((2-ethylhexyl)(hexyl)amino)-4-((2-ethylhexyl)oxy)phenyl)phosphoramidate.

(E)-diethyl(2-((2-bromo-4-cyanophenyl)diazenyl)-5-((2-ethylhexyl)(hexyl)amino)-4-((2-ethylhexyl)oxy)phenyl)phosphoramidate A mixture of 4-amino-3-bromobenzonitrile (2.07 g, 10.51 mmol), 25 mL acetic acid and 5 mL propionic acid was stirred for 15 min. The resulting solution was cooled in ice and nitrosylsulfuric acid (40% solution in sulphuric acid; 3.32 g, 10.46 mmol) was added over a 20 min period at 4-6° C. The addition funnel was flushed with 5 mL acetic acid, then the amide diethyl(3-((2-ethylhexyl)(hexyl)amino)-4-((2-ethylhexyl)oxy)phenyl)phosphoramidate (4.40 g, 7.73 mmol), dissolved in 20 mL acetic acid, was added over a 5 min period at 3-5° C. The mixture was stirred for 1 h, allowing the temperature to rise to 10° C. The resulting suspension was cooled with ice and 12 mL 30% sodium hydroxide was added over a 15 min period at 8 to 16° C. The cooling bath was removed when the temperature had dropped to 10° C. After stirring for 1 h there was added 25 mL dioxane and the red-brown mixture was stirred for an additional hour at RT. 75 mL water was added and the mixture was extracted with 3×100 mL toluene, the successive organic layers being washed with 50 mL water. Drying and rotary evaporation yielded a residue which was purified by chromatography on 100 g silica. Elution with heptane, containing increasing amounts of toluene and ethyl acetate yielded the product (E)-diethyl(2-((2-bromo-4-cyanophenyl)diazenyl)-5-((2-ethylhexyl)(hexyl)amino)-4-((2-ethylhexyl)oxy)phenyl)phosphoramidate as a red-magenta oil.

(E)-diethyl(2-((2,4-dicyanophenyl)diazenyl)-5-((2-ethylhexyl)(hexyl)amino)-4-((2-ethylhexyl)oxy)phenyl)phosphoramidate The product (E)-diethyl(2-((2-bromo-4-cyanophenyl)diazenyl)-5-((2-ethylhexyl)(hexyl)amino)-4-((2-ethylhexyl)oxy)phenyl)phosphoramidate was stirred for 8 h at 50° C. with 25 mL dimethyl sulphoxide (DMSO) and copper(I) cyanide (1.70 g, 19.0 mmol). The mixture was poured in 75 mL dilute ammonia and extraction was performed with 2×150 mL toluene. The successive organic layers were washed with 30 mL water, dried and rotary evaporated. The residue (2.20 g) was chromatographed on 75 g silica, elution being done with heptane containing increasing amounts of ethyl acetate. The product fractions were combined to give the desired purple (E)-diethyl(2-((2,4-dicyanophenyl)diazenyl)-5-((2-ethylhexyl)(hexyl)amino)-4-((2-ethylhexyl)oxy)phenyl)phosphoramidate.

In another example of a dye compound according to Formula 1, the dye compound has the following formula:

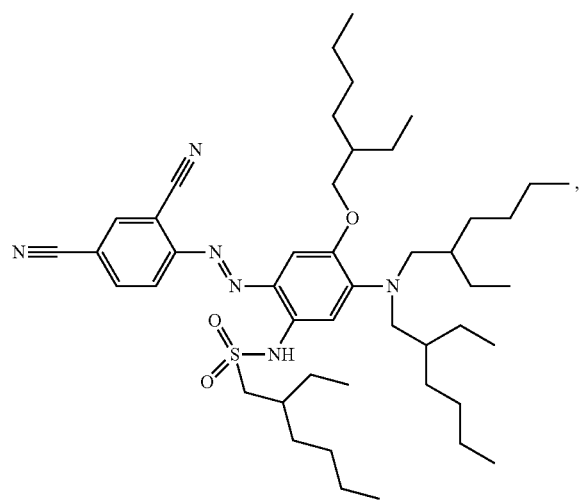 [SMILES: CCCCC(CC)COc1cc(/N=N/c2ccc(C#N)cc2C#N)c(NS(=O)(=O)CC(CC)CCCC)cc1N(CC(CC)CCCC)CC(CC)CCCC]

This compound is N-{5-[bis(2-ethylhexyl)amino]-2-[(E)-2-(2,4-dicyanophenyl)diazen-1-yl]-4-[(2-ethylhexyl)oxy]phenyl}-2-ethylhexane-1-sulfonamide.

In another example of a dye compound according to Formula 1, the dye compound has the following formula:

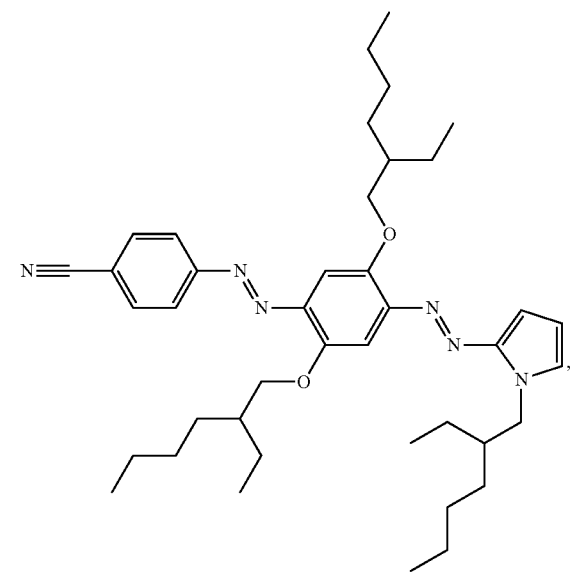 [SMILES: CCCCC(CC)COc1cc(/N=N/c2cccn2CC(CC)CCCC)c(OCC(CC)CCCC)cc1/N=N/c1ccc(C#N)cc1]

This compound is 4-[(E)-2-{4-[(E)-2-[1-(2-ethylhexyl)-1H-pyrrol-2-yl]diazen-1-yl]-2,5-bis[(2-ethylhexyl)oxy]phenyl}diazen-1-yl]benzonitrile.

In another example of a dye compound according to Formula 1, the dye compound has the following formula:

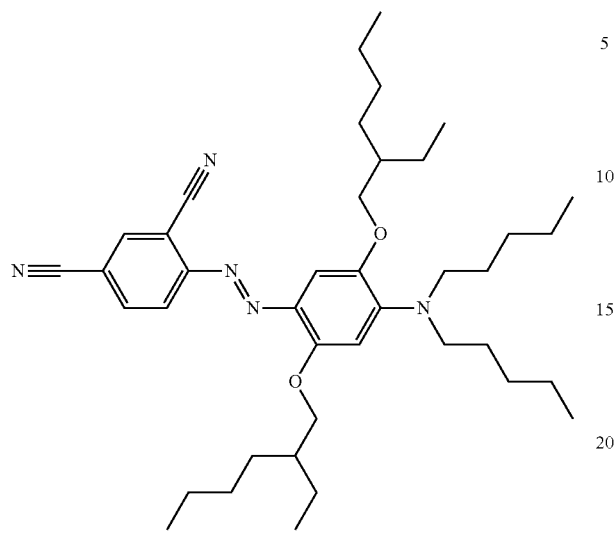

This compound 4-[(E)-2-[4-(dipentylamino)-2,5-bis[(2-ethylhexyl)oxy]phenyl]diazen-1-yl]benzene-1,3-dicarbonitrile may be synthesised as follows:

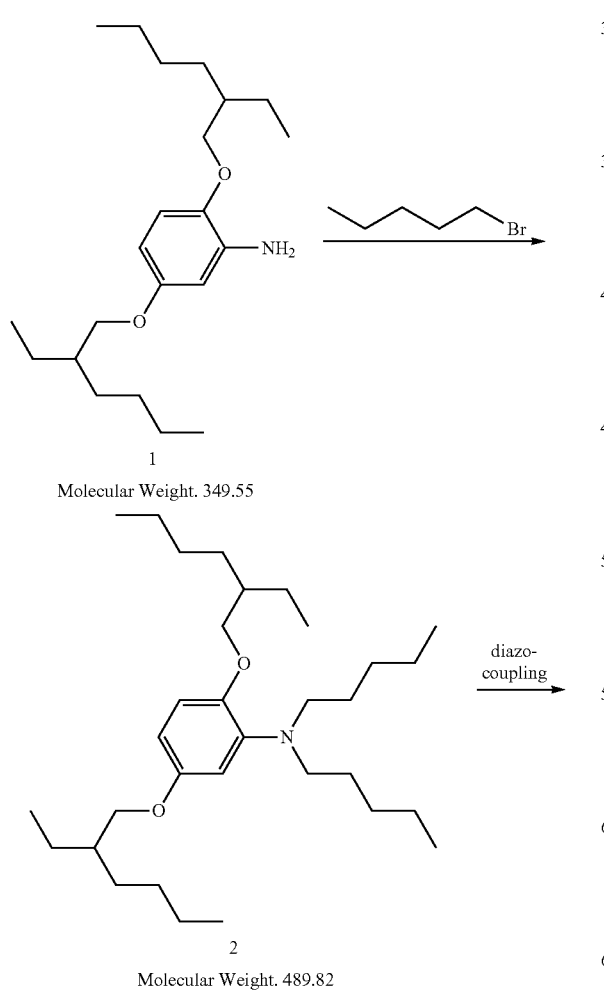

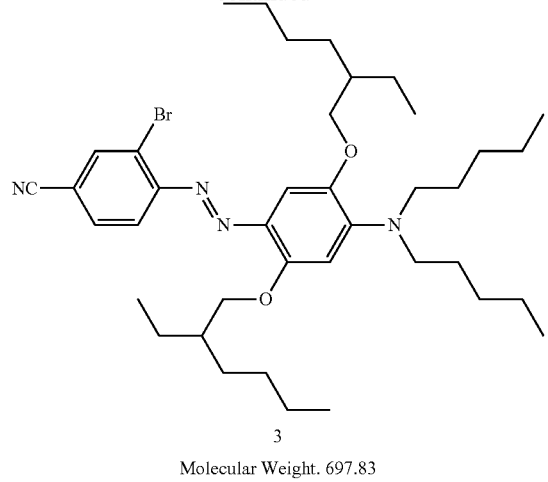 [SMILES: CCCCCN(CCCCC)c1cc(OCC(CC)CCCC)c(/N=N/c2ccc(C#N)cc2C#N)cc1OCC(CC)CCCC]

3
Molecular Weight. 697.83

↓ CuCN

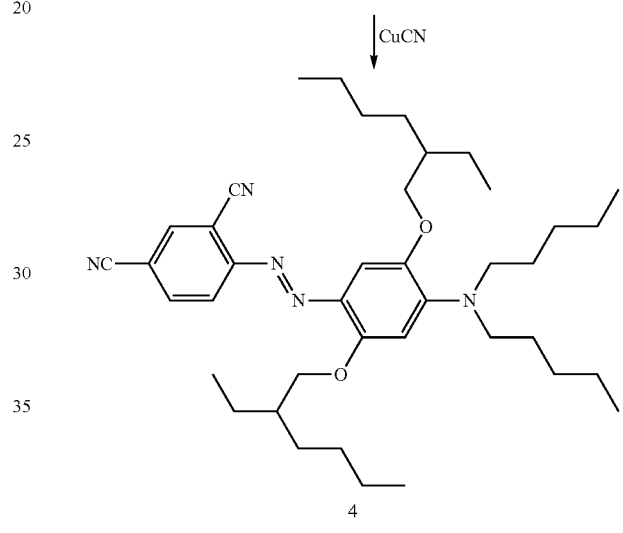

4
Molecular Weight: 643.94

2,5-Bis((2-ethylhexyl)oxy)-N,N-dipentylaniline 2,5-Bis((2-ethylhexyl)oxy)-aniline (5 g, 14.3 mmol, 1 eq) was mixed with bromopentane (13 g, 86 mmol, 6 eq), K₂CO₃ (6 g, 43 mmol, 3 eq) and tetrabutylammoniumbromide (0.1 g). The reaction mixture was stirred for 5 min at RT. The mixture was heated to 100° C. and stirred for 48 h. Temperature was increased to 115° C. and bromopentane (4.3 g, 29 mmol, 2 eq) was added. After stirring for 71 h full conversion was obtained. Reaction mixture was cooled to RT, mixed with EtOAc (50 mL), washed with water (2×50 mL), dried (Na₂SO₄) and concentrated. After distillation (Kugelrohr, 1 mbar, 100° C., 2 h, removal of bromopentane) the product 2,5-bis((2-ethylhexyl)oxy)-N,N-dipentylaniline (6.8 g, 97% isolated yield) was obtained as a brown oil.

3-bromo-4 [(E)-2-[4-(dipentylamino)-2,5-bis[(2-ethylhexyl)oxy]phenyl]diazen-1-yl]benzonitrile 2-Bromo-4-cyanoaniline (3.8 g, 19.5 mmol, 1.4 eq) was mixed with propionic acid (7.5 mL) and acetic acid (28 mL). The mixture was stirred for 40 min. at room temperature and a yellow solution was obtained. The solution was cooled to 0° C. Nitrosylsulfuric acid (6.2 g, 19.5 mmol, 1.4 eq, 40% sulfuric acid) was added dropwise within 20 min. and the temperature was kept between 0-3° C. The clear yellow solution was added dropwise to a solution of 2,5-bis((2-ethylhexyl)oxy)-N,N-dipentylaniline (6.8 g, 13.0 mmol, 1 eq), 1.4 dioxane (45 mL) and acetic acid (9.5 mL) within 15 min. and the temperature was kept between 0-2° C. Stirring was continued for 2.5 h, and then the ice bath was removed. While warming to room temperature the reaction was stirred for another 1.5 h. Afterwards the mixture was cooled with an ice bath and NaOH solution (NaOH, 33 w %, 10 mL, water 60 mL) was added within 20 min. while the temperature was kept between 7-9° C. The mixture was stirred for 5 min. and poured into a solution of toluene (200 mL) and water (100 mL). The organic layer was separated, washed with water (50 mL). The aqueous layers were combined, washed with toluene (3×100 mL). The organic layers were combined, dried on Na₂SO₄, filtered and concentrated. After purification by column chromatography (silicagel, 10% EtOAc/heptane) 3-bromo-4-[(E)-2-[4-(dipentylamino)-2,5-bis[(2-ethylhexyl)oxy]phenyl]diazen-1-yl]benzonitrile (4.6 g, 6.7 mmol, 51% yield) was isolated as a red oil.

4-[(E)-2-[4-(dipentylamino)-2,5-bis[(2-ethylhexyl) oxy]phenyl]diazen-1-yl]benzene-1,3-dicarbonitrile 3-Bromo-4-[(E)-2-[4-(dipentylamino)-2,5-bis[(2-ethylhexyl)oxy]phenyl]diazen-1-yl]benzonitrile (3 g, 4.3 mmol, 1 eq) was dissolved in DMF (50 mL). CuCN (967 mg) was added and the mixture was heated to 100° C. The reaction mixture was cooled to RT and NH₃ solution was added. The mixture was extracted with toluene (3×60 mL), the organic layer was washed with water (3×60 mL) and concentrated. The product was purified with column chromatography (silicagel, 5% EtOAc/heptane) to afford 4-[(E)-2-[4-(dipentylamino)-2,5-bis[(2-ethylhexyl)oxy]phenyl]diazen-1-yl]benzene-1,3-dicarbonitrile (800 mg, 29% yield) as a purple solid.

In another example of a dye compound according to Formula 1, the dye compound has the following formula:

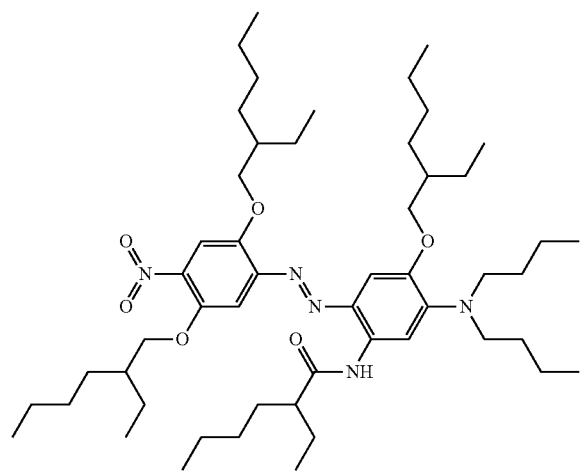 [SMILES: CCCCC(CC)COc1cc([N+](=O)[O-])c(OCC(CC)CCCC)cc1/N=N/c1cc(OCC(CC)CCCC)c(N(CCCC)CCCC)cc1NC(=O)C(CC)CCCC]

This compound is N-{2-[(E)-2-{2,5-bis[(2-ethylhexyl)oxy]-4-nitrophenyl}diazen-1-yl]-5-(dibutylamino)-4-[(2-ethylhexyl)oxy]phenyl}-2-ethylhexanamide.

In another example of a dye compound according to Formula 1, the dye compound has the following formula:

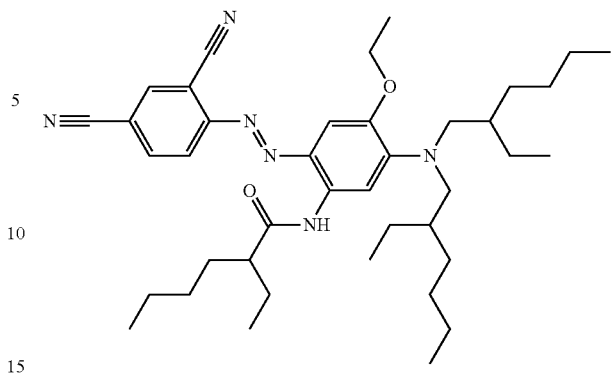

This compound is (E)-N-(5-(bis(2-ethylhexyl)amino)-2-((2,4-dicyanophenyl)diazenyl)-4-ethoxyphenyl)-2-ethylhexanamide may be synthesised as follows:

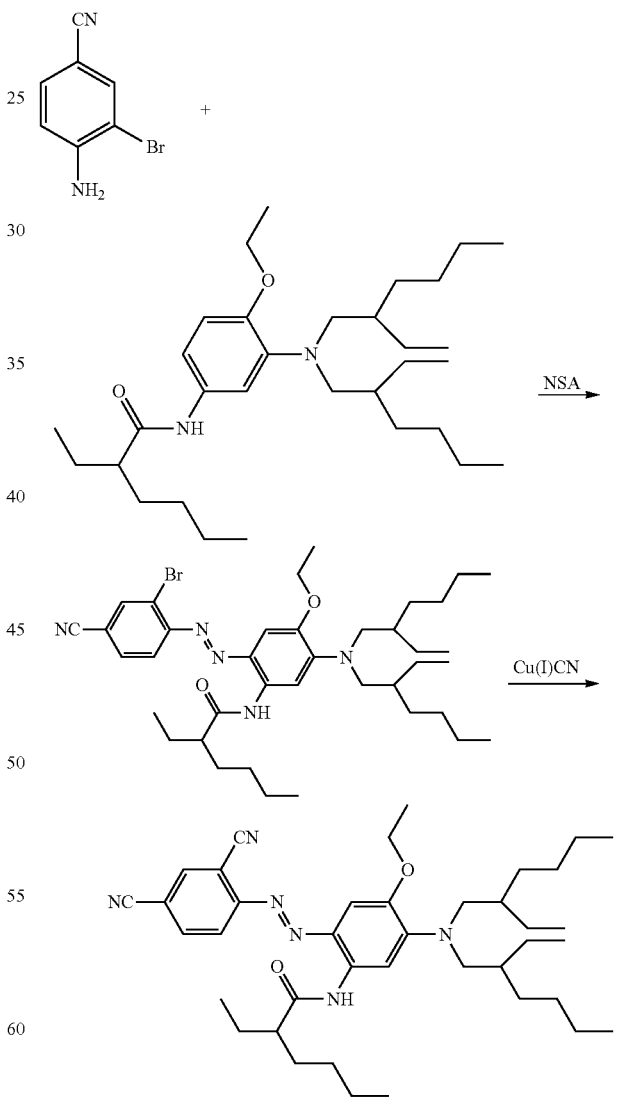

A suspension of 4-Amino-3-bromobenzonitrile (15.0 g, 76.1 mmol) in a mixture of AcOH (120 mL) and EtCO₂H (80 mL) was warmed until a clear solution was obtained and then cooled to 8° C. with an ice bath. 40% nitrosyl sulfuric acid (14.3 mL, 83.7 mmol) was added drop wise. The mixture was stirred 1 h at 7° C. and then added slowly to a solution of N-{3-[bis(2-ethylhexyl)amino]-4-ethoxyphenyl}-2-ethylhexanamide (35.0 g, 69.6 mmol) in 1,4-dioxane (120 mL) and acetic acid (30 mL) cooled in an ice bath. The mixture was stirred at 7° C. during 1 h and then hydrolyzed by drop wise addition of 33% NaOH (75 mL) while cooling in an ice bath. After 30 minutes, the mixture was poured into water and extracted with toluene. The combined organic layers were washed with water and the solvent evaporated. Purification by column chromatography (silicagel, heptane/EtOAc 60/1) afforded (E)-N-(5-(bis(2-ethylhexyl)amino)-2-((2-bromo-4-cyanophenyl)diazenyl)-4-ethoxyphenyl)-2-ethylhexanamide (35 g).

This was dissolved in dimethylformamide DMF (400 mL) and copper(I) cyanide (17.6 g, 196.9 mmol) was added while the mixture was cooled in a water bath. After 20 h of stirring at RT, the reaction mixture was poured into 15% ammonia and extracted with toluene (3×). The combined organic layers were washed with ammonia, water and dried with Na$_2$SO$_4$. After evaporation of the solvent the residue was purified by column chromatography (silicagel, heptane/EtOAc 80/1 to 30/1) to obtain (E)-N-(5-(bis(2-ethylhexyl)amino)-2-((2,4-dicyanophenyl)diazenyl)-4-ethoxyphenyl)-2-ethylhexanamide (19.8 g, 39% yield) as a purple oil.

In another example of a dye compound according to Formula 1, the dye compound has the following formula:

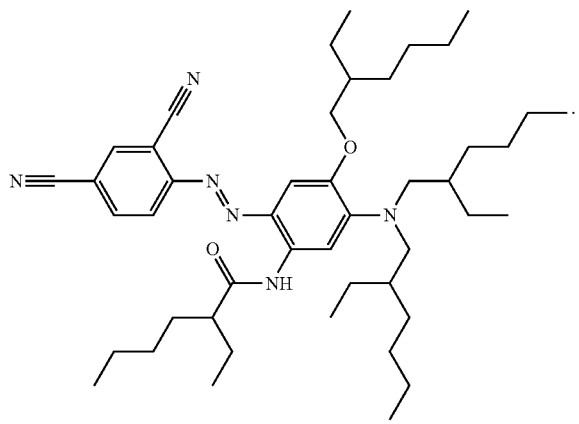 [SMILES: CCCCC(CC)COc1cc(/N=N/c2ccc(C#N)cc2C#N)c(NC(=O)C(CC)CCCC)cc1N(CC(CC)CCCC)CC(CC)CCCC]

In a further example of a dye compound according to Formula 1, the dye compound has the following formula:

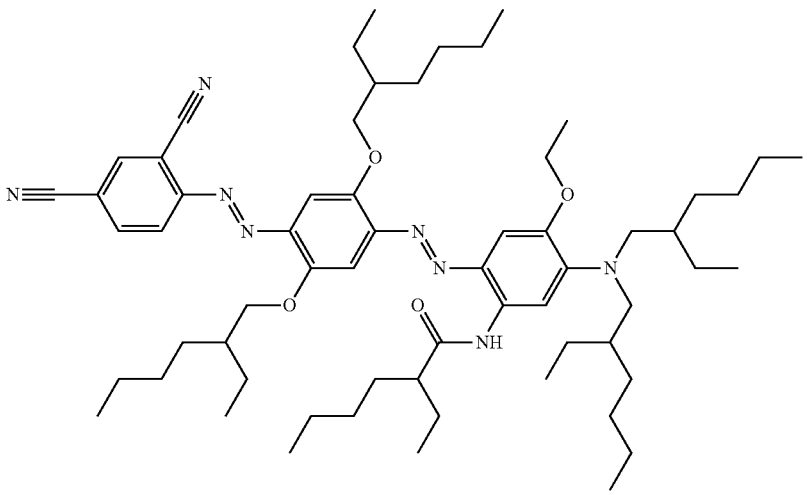 [SMILES: CCCCC(CC)COc1cc(/N=N/c2cc(OCC)c(N(CC(CC)CCCC)CC(CC)CCCC)cc2NC(=O)C(CC)CCCC)c(OCC(CC)CCCC)cc1/N=N/c1ccc(C#N)cc1C#N]

In further examples, the fluid for an electrowetting apparatus, such as that described above, includes at least one dye compound having the following formula:

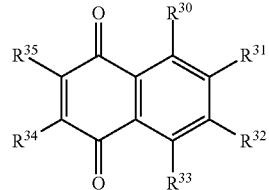

(Formula 2)

where R30 is selected from: OH, or an amino group having the formula —N(R$^q$)(R$^r$), with R$^q$ being H and R$^r$ being an alkyl group (such a secondary amino group gives greater solubility in the carrier fluid compared with a primary amine and a greater stability and colour intensity than a tertiary amino group); an alkoxy group having the formula —O—R$^{ae}$, with R$^{ae}$ being an alkyl group; or a thioalkyl group having the formula —S—R$^{af}$, with R$^{af}$ being an alkyl group, R31 is selected from: H, or has the formula —X—Y, where X is selected from: —S—, a single bond, or —O—; Y is selected from: —R$^s$, or —R$^A$, where R$^s$ is an alkyl group and R$^A$ is an aryl group; R$^{32}$ is H; R$^{33}$ is selected from: an amino group having the formula —N(R$^t$)(R$^u$), with R$^t$ being H and Ru being an alkyl group (such a secondary amino group has similar benefits as the amino group of R$^{30}$), an alkoxy group having the formula —O—R$^{af}$, with R$^{af}$ being an alkyl group, or a thioalkyl group having the formula —S—R$^{ag}$, with R$^{ag}$ being an alkyl group; R$^{34}$ and R$^{35}$ are selected from the following: R$^{34}$ and R$^{35}$ are each H, or together R$^{34}$ and R$^{35}$ form:

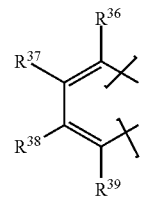

where $R^{36}$, $R^{38}$ and $R^{39}$ are each independently selected from: H, or an alkyl group; $R^{37}$ is selected from: H, an alkyl group, or an ester group having the formula —COO—$R^{ah}$, where $R^{ah}$ is an alkyl group In examples, the alkyl group of one or more of: $R^q$, $R^r$, $R^{ae}$, $R^{af}$, $R^s$, $R^t$, $R^u$, $R^{af}$, $R^{ag}$, $R^{36}$, $R^{38}$, $R^{39}$, $R^{37}$, $R^{ah}$, is independently selected from: a straight chain alkyl group having 1 to 22 carbon atoms, a branched alkyl group having 3 to 22 carbon atoms, or a cyclic alkyl group having 5 to 22 carbon atoms.

Further, or in further examples where the dye compound is according to Formula 2, the dye compound is selected from:

a formula where: $R^{30}$ is OH, R31 has the formula —X—Y where X is a single bond and Y is —$R^s$ where —$R^s$ is selected from: an alkyl group having 1 to 22 carbon atoms, a straight chain alkyl group having 1 to 22 carbon atoms, a straight chain alkyl group having 1 to 8 carbon atoms, a straight chain alkyl group having 8 carbon atoms, a branched alkyl group having 3 to 22 carbon atoms, a branched alkyl group having 3 to 8 carbon atoms, a branched alkyl group having 8 carbon atoms, or a branched alkyl group having the formula:

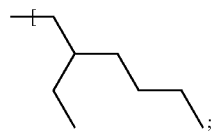

$R^{33}$ is the amino group having the formula —N($R^t$)($R^u$), with $R^t$ being H and $R^u$ being an alkyl group selected from: an alkyl group having 1 to 22 carbon atoms, a straight chain alkyl group having 1 to 22 carbon atoms, a straight chain alkyl group having 1 to 8 carbon atoms, a straight chain alkyl group having 8 carbon atoms, a branched alkyl group having 3 to 22 carbon atoms, a branched alkyl group having 3 to 8 carbon atoms, a branched alkyl group having 8 carbon atoms, or a branched alkyl group having the formula:

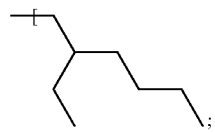

$R^{34}$ and $R^{35}$ together form:

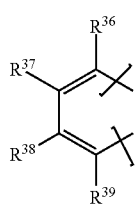

where $R^{36}$, $R^{37}$, $R^{38}$ and $R^{39}$ are each H, or a formula where: $R^{30}$ is the amino group having the formula —N($R^q$)($R^r$), with $R^q$ being H and $R^r$ being an alkyl group selected from: an alkyl group having 1 to 22 carbon atoms, a straight chain alkyl group having 1 to 22 carbon atoms, a straight chain alkyl group having 1 to 8 carbon atoms, a straight chain alkyl group having 8 carbon atoms, a branched alkyl group having 3 to 22 carbon atoms, a branched alkyl group having 3 to 8 carbon atoms, a branched alkyl group having 8 carbon atoms, or a methyl alkyl group; $R^{31}$ has the formula —X—Y where X is —S— and Y is $R^s$ being an alkyl group selected from: an alkyl group having 1 to 22 carbon atoms, a straight chain alkyl group having 1 to 22 carbon atoms, a straight chain alkyl group having 1 to 12 carbon atoms, a straight chain alkyl group having 12 carbon atoms, a branched alkyl group having 3 to 22 carbon atoms, a branched alkyl group having 3 to 12 carbon atoms, a branched alkyl group having 12 carbon atoms, or a branched alkyl group having the formula:

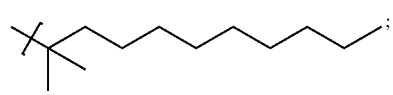

$R^{33}$ is the amino group having the formula —N($R^t$)($R^u$), with $R^t$ being H and $R^u$ being an alkyl group selected from: an alkyl group having 1 to 22 carbon atoms, a straight chain alkyl group having 1 to 22 carbon atoms, a straight chain alkyl group having 1 to 8 carbon atoms, a straight chain alkyl group having 8 carbon atoms, a branched alkyl group having 3 to 22 carbon atoms, a branched alkyl group having 3 to 8 carbon atoms, a branched alkyl group having 8 carbon atoms, or a branched alkyl group having the formula:

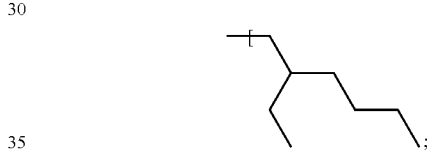

$R^{34}$ and $R^{35}$ together form:

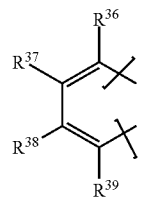

where $R^{36}$, $R^{37}$, $R^{38}$ and $R^{39}$ are each H.

In an example of a dye compound according to Formula 2, the dye compound has the following formula:

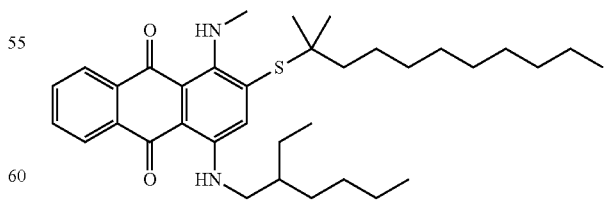

This compound is 4-[(2-ethylhexyl)amino]-1-(methylamino)-2-[(2-methylundecan-2-yl)sulfanyl]-9,10-dihydroanthracene-9,10-dione.

In another example of a dye compound according to Formula 2, the dye compound has the following formula:

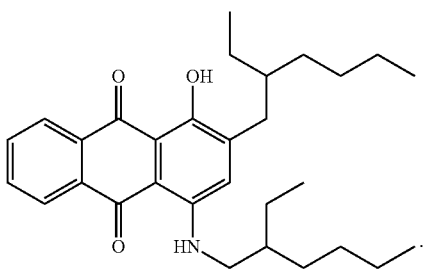 [SMILES: CCCCC(CC)CNc1cc(CC(CC)CCCC)c(O)c2c1C(=O)c1ccccc1C2=O]

This compound 2-(2-ethylhexyl)-4-[(2-ethylhexyl)amino]-1-hydroxy-9,10-dihydroanthracene-9,10-dione may be synthesised as follows:

346 g of leucoquinizarin was reacted with 186 g of 2-ethylhexylamine in dichloromethane. After stirring for 24 h, the mixture was rotary evaporated and 520 g of 2-ethyl-hexanal in isopropanol was added to the residual imine with cooling, followed by addition of 316 g piperidinium acetate in isopropanol. After stirring for 48 h at 70 to 85° C., the mixture was worked up and the crude product was chromatographed. This resulted in a total yield of 336 g of the desired product 2-(2-ethylhexyl)-4-[(2-ethylhexyl)amino]-1-hydroxy-9,10-dihydroanthracene-9,10-dione (51% yield).

In further examples, the fluid for an electrowetting apparatus, such as that described above, includes at least one dye compound having the following formula:

(Formula 3)

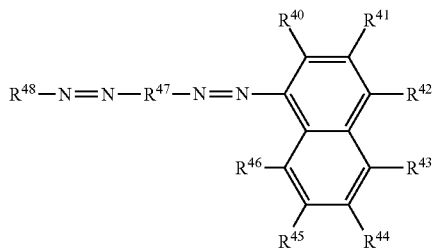

where each of $R^{40}$, $R^{41}$, $R^{42}$, $R^{43}$, $R^{44}$, $R^{45}$, $R^{46}$ is independently selected from: H, an alkoxy group, an alkyl group, or an amino group having the formula —N(R$^v$)(R$^w$), with each of R$^v$ and R$^w$ independently being an alkyl group for a tertiary amino group or one of R$^v$ and R$^w$ being H and the other one of R$^v$ and R$^w$ being an alkyl group for a secondary amino group (a primary amino group is not sufficiently soluble in the carrier fluid); where $R^{47}$ is an arylene group and $R^{48}$ is an aryl group.

In examples, the alkyl group of one or more of: $R^{40}$, $R^{41}$, $R^{42}$, $R^{43}$, $R^{44}$, $R^{45}$, $R^{46}$, R$^v$, R$^w$ is independently selected from: a straight chain alkyl group having 1 to 22 carbon atoms, a branched alkyl group having 3 to 22 carbon atoms, or a cyclic alkyl group having 5 to 22 carbon atoms.

Further, or in further examples where the dye compound is according to Formula 3, $R^4$, $R^{41}$, $R^{42}$, $R^{43}$, $R^{44}$, $R^{45}$, $R^{46}$ are each independently selected from: H, a straight chain alkyl group having 1 to 22 carbon atoms, a branched alkyl group having 3 to 22 carbon atoms, or an amino group having the formula —N(R$^v$)(R$^w$), with each of R$^v$ and R$^w$ independently being selected from: H, or an alkyl group having 1 to 22 carbon atoms, or a branched alkyl group having 3 to 22 carbon atoms; $R^{47}$ has the formula:

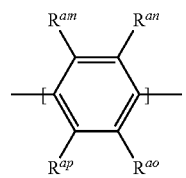

where each of $R^{am}$, $R^{an}$, $R^{ao}$, $R^{ap}$ is independently selected from: H, a straight chain alkyl group having 1 to 22 carbon atoms, or a branched alkyl group having 3 to 22 carbon atoms; $R^{48}$ has the formula:

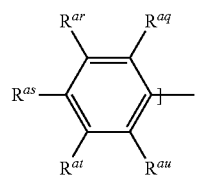

where each of $R^{aq}$, $R^{ar}$, $R^{at}$, is independently selected from: H, a straight chain alkyl group having 1 to 22 carbon atoms, a halogen atom, or a branched alkyl group having 3 to 22 carbon atoms, wherein $R^{as}$ is selected from: H, a straight chain alkyl group having 1 to 22 carbon atoms, a halogen atom, an ester group, or a branched alkyl group having 3 to 22 carbon atoms, wherein $R^{au}$ is selected from: H, a straight chain alkyl group having 3 to 22 carbon atoms, a halogen atom, a cyano group, a nitro group, or a branched alkyl group having 3 to 22 carbon atoms.

In further examples, the fluid for an electrowetting apparatus, such as that described above, includes at least one dye compound having the following formula:

(Formula 4)

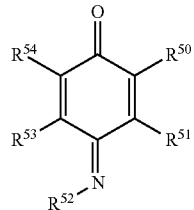

where $R^{50}$ and $R^{51}$ are independently selected from: H, or an amide group having the formula —NH—C(=O)R$^{aj}$ with R$^{aj}$ being selected from H, or an alkyl group, or together $R^{50}$ and $R^{51}$ form:

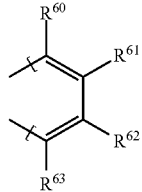

where each of $R^{60}$, $R^{61}$, $R^{62}$, $R^{63}$ is independently H or an alkyl group; $R^{53}$ and $R^{54}$ are selected from the following: $R^{53}$ and $R^{54}$ are each H, or together $R^{53}$ and $R^{54}$ form:

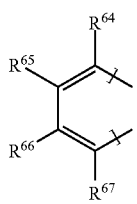

where each of $R^{64}, R^{65}, R^{66}, R^{67}$ is independently H or an alkyl group; $R^{52}$ has the formula:

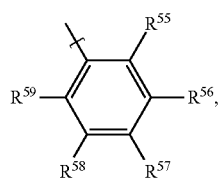

where $R^{55}$ is selected from: an alkoxy group having the formula —O—$R^x$, where $R^x$ is an alkyl group, an alkyl group, or a halogen atom; $R^{57}$ is an amino group having the formula —N($R^y$)($R^z$), with each of $R^y$ and $R^z$ independently being selected from: H, or an alkyl group; each of $R^{56}, R^{58}$ and $R^{59}$ is independently selected from: H, or an alkyl group.

In examples, the alkyl group of one or more of: $R^{aj}, R^{ak}, R^{60}, R^{61}, R^{62}, R^{63}, R^{64}, R^{65}, R^{66}, R^{67}, R^x, R^{55}, R^y, R^z, R^{56}, R^{58}$, or $R^{59}$ is independently selected from: a straight chain alkyl group having 1 to 22 carbon atoms, a branched alkyl group having 3 to 22 carbon atoms, or a cyclic alkyl group having 5 to 22 carbon atoms.

Further, or in further examples where the dye compound is according to Formula 4, $R^{50}$ and $R^{51}$ are each H, $R^{53}$ and $R^{54}$ together form:

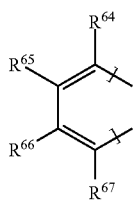

where each of $R^{64}, R^{65}, R^{66}, R^{67}$ is H, and $R^{52}$ has the formula:

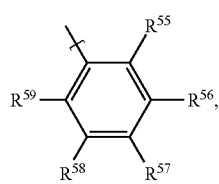

where $R^{55}$ is the alkoxy group having the formula —O—$R^x$, where $R^x$ is an alkyl group selected from: an alkyl group having 1 to 22 carbon atoms, a straight chain alkyl group having 1 to 22 carbon atoms, a straight chain alkyl group having 1 to 8 carbon atoms, a straight chain alkyl group having 8 carbon atoms, a branched alkyl group having 3 to 22 carbon atoms, a branched alkyl group having 3 to 8 carbon atoms, a branched alkyl group having 8 carbon atoms, or a branched alkyl group having the formula:

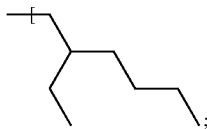

$R^{56}, R^{58}$ and $R^{59}$ are H, and $R^{57}$ is the amino group having the formula —N($R^y$)($R^z$), with each of $R^y$ and $R^z$ independently being selected from: H, or an alkyl group selected from: an alkyl group having 1 to 22 carbon atoms, a straight chain alkyl group having 1 to 22 carbon atoms, a straight chain alkyl group having 1 to 8 carbon atoms, a straight chain alkyl group having 8 carbon atoms, a branched alkyl group having 3 to 22 carbon atoms, a branched alkyl group having 3 to 8 carbon atoms, a branched alkyl group having 8 carbon atoms, or a branched alkyl group having the formula:

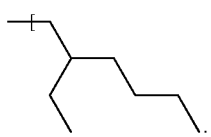

Further, or in further examples where the dye compound is according to Formula 4, the dye compound is selected from:

a formula where $R^{50}, R^{51}, R^{53}$ are each H; $R^{54}$ is the amide group having the formula —NH—C(=O)($R^{aj}$) with $R^{aj}$ being selected from H, or an alkyl group selected from: an alkyl group having 1 to 22 carbon atoms, a straight chain alkyl group having 1 to 22 carbon atoms, a straight chain alkyl group having 1 to 8 carbon atoms, a straight chain alkyl group having 8 carbon atoms, a branched alkyl group having 3 to 22 carbon atoms, a branched alkyl group having 3 to 8 carbon atoms, a branched alkyl group having 8 carbon atoms, a methyl group, or a branched alkyl group having the formula:

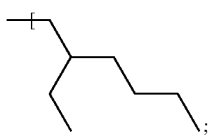

$R^{55}$ is an alkyl group selected from: an alkyl group having 1 to 22 carbon atoms, a straight chain alkyl group having 1 to 22 carbon atoms, a straight chain alkyl group having 1 to 8 carbon atoms, a straight chain alkyl group having 8 carbon atoms, a branched alkyl group having 3 to 22 carbon atoms, a branched alkyl group having 3 to 8 carbon atoms, a branched alkyl group having 8 carbon atoms, or a methyl group; $R^{56}, R^{58}$ and $R^{59}$ are H; $R^{57}$ is an alkyl group selected from: an alkyl group having 1 to 22 carbon atoms, a straight chain alkyl group having 1 to 22 carbon atoms, a straight chain alkyl group having 1 to 8 carbon atoms, a straight chain alkyl group having 8 carbon atoms, a branched alkyl group having 3 to 22 carbon atoms, a branched alkyl group having 3 to 8 carbon atoms, a branched alkyl group having 8 carbon atoms, or a branched alkyl group having the formula:

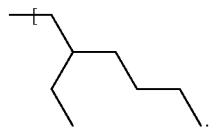

In an example of a dye compound according to Formula 4, the dye compound has the following formula:

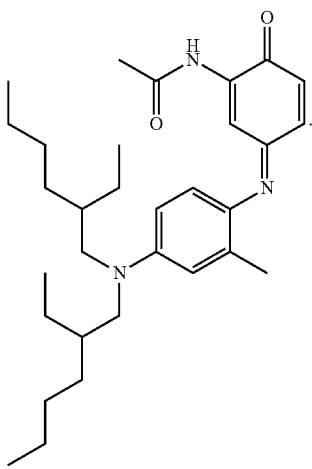 [SMILES: CCCCC(CC)CN(CC(CC)CCCC)c1ccc(/N=C2/C=CC(=O)C(NC(C)=O)=C2)c(C)c1]

This compound N-[3-({4-[bis(2-ethylhexyl)amino]-2-methylphenyl}imino)-6-oxocyclohexa-1,4-dien-1-yl]acetamide may be synthesised as follows:

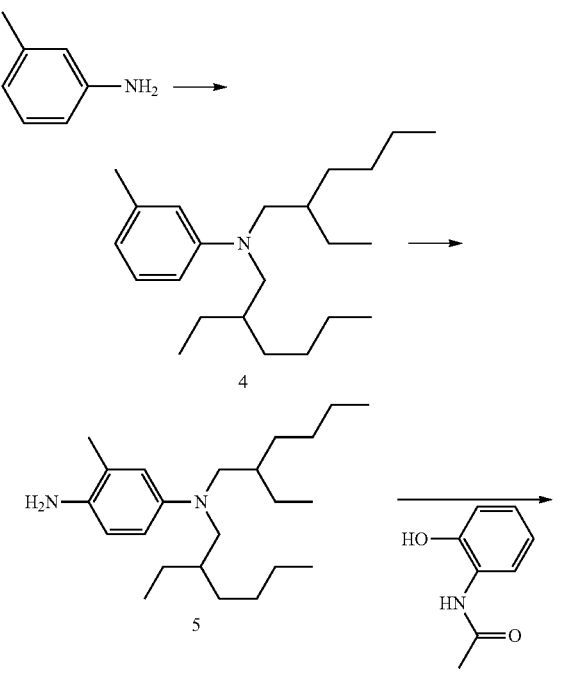

-continued

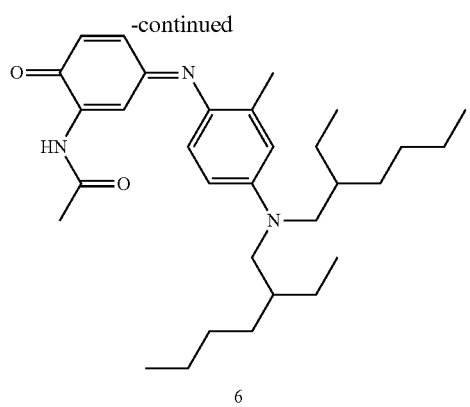

N,N-bis(2-ethylhexyl)-3-methylaniline

A mixture of 3-methylaniline (10.70 g, 0.100 mol), 2-ethylhexyl bromide (81.0 g, 0.420 mol) and potassium carbonate (40.0 g, 0.290 mol) was heated for 3 d at 105° C. and 10 d at 122° C. Additional potassium carbonate (10.0 g) and 2-ethylhexyl bromide (20 mL) were added and heating was continued for 3 d. After cooling, 150 mL heptane was added and the mixture was filtered and washed with heptane. Rotary evaporation of the filtrate, followed by Kugelrohr distillation gave a fraction which contained a considerable amount of the monoalkyl compound, followed by 7.14 g of the dialkyl compound N,N-bis(2-ethylhexyl)-3-methylaniline.

N,N-bis(2-ethylhexyl)-3-methylbenzene-1,4-diamine

A solution of sodium nitrite (3.45 g, 50.0 mmol) in 10 mL water was added over a 20 min period and at 4-8° C. to an ice-cooled solution of N,N-bis(2-ethylhexyl)-3-methylaniline (15.15 g, 45.7 mmol) in 30 mL acetic acid and 20 mL conc. hydrochloric acid. The mixture was stirred for 45 min in the cold bath and then it was poured in 100 mL water. The product was extracted with 2×150 mL toluene/dichloromethane (6/1). The successive organic layers were washed with 75 mL water, dried and rotary evaporated.

The residue was dissolved in 150 mL THF, the solution was cooled with ice and lithium aluminium hydride (3.0 g, 88.2 mmol) was added in small portions. The mixture was heated under reflux for 2 h after addition of the hydride. An additional 1.0 g lithium aluminium hydride was added and reflux was continued for 1½ h. After stirring overnight, the mixture was slowly treated with 10 mL 33% sodium hydroxide solution. Some sodium sulphate was added, the mixture was stirred for 15 min, filtered and washed with THF. The filtrate was rotary evaporated and the residue was used as such in the next step.

N-[3-({4-[bis(2-ethylhexyl)amino]-2-methylphenyl}imino)-6-oxocyclohexa-1,4-dien-1-yl]acetamide Sodium bicarbonate (3.60 g, 42.86 mmol) was added to a solution of 2-acetamidophenol (1.59 g, 10.53 mmol) in 100 mL ethyl acetate and 25 mL ethanol, followed by 15 mL water. The mixture was stirred for 5 min, then N,N-bis(2-ethylhexyl)-3-methylbenzene-1,4-diamine (5.50 g, 15.9 mmol if pure) was added. The mixture was cooled in ice and a solution of potassium hexacyanoferrate (14.15 g, 42.98 mmol) in 60 mL water was added over a 15 min period at 2-8° C. The cooling bath was removed after 5 min and the greenish mixture was stirred for 40 min (internal temperature reached 14° C.). The mixture was poured in 50 mL water and extracted with 2×150 mL heptane/ethyl acetate. The successive organic layers were washed with 50 mL water, dried and rotary evaporated. The residue was chromatographed on 50 g silicagel, elution being done with heptane containing increasing amounts of ethyl acetate. The blue fractions were checked for purity by TLC and the pure fractions were combined to yield 1.13 g of N-[3-({4-[bis(2-ethylhexyl)amino]-2-methylphenyl}imino)-6-oxocyclohexa-1,4-dien-1-yl]acetamide as a solidifying blue oil.

The above examples are to be understood as illustrative examples. Further examples are envisaged. It is to be understood that any feature described in relation to any one example may be used alone, or in combination with other features described, and may also be used in combination with one or more features of any other of the examples, or any combination of any other of the examples. Furthermore, equivalents and modifications not described above may also be employed without departing from the scope of the accompanying claims.

What is claimed is:

1. An electrowetting apparatus comprising:
   a fluid comprising:
   (i) at least one dye compound with the formula:

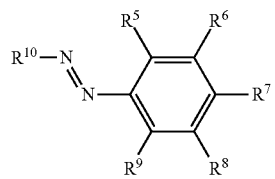

(Formula 1)

wherein $R^5$ is H;
$R^6$ is an alkoxy group having the formula —O—$R^a$, wherein $R^a$ is an alkyl group;
$R^8$ is H;
$R^9$ is:
  an alkoxy group having the formula —O—$R^d$, wherein $R^d$ is an alkyl group;
  an amide group having the formula —NHC(=O)$R^e$, wherein $R^e$ is an alkyl group;
  a sulphonamide group having the formula —NH—S(=O)(=O)—$R^f$, wherein $R^f$ is an alkyl group, or
  an amidophosphate group having the formula —NH—P(=O)(—O—$R^g$)$_2$, wherein $R^g$ is independently an alkyl group,
$R^{10}$ has the formula B-A-,
  wherein B has the formula:

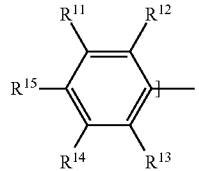

wherein $R^{11}$ is H;

$R^{13}$ is:
  H,
  a cyano group having the formula —CN,
  an alkyl group $R^i$, or
  a halogen atom;
$R^{14}$ is:
  H,
  a cyano group having the formula —CN,
  a nitro group having the formula —NO$_2$, or
  an alkoxy group having the formula —O—$R^k$, wherein $R^k$ is an alkyl group;
a) $R^7$ is:
  N=N-Het$^1$ wherein Het$^1$ is a heterocyclic group;
$R^{12}$ is:
  H,
  a cyano group having the formula —CN,
  an alkoxy group having the formula —O—$R^h$, wherein $R^h$ is an alkyl group,
  an alkyl group $R^i$, or
  a halogen atom;
$R^{15}$ is:
  a cyano group having the formula —CN,
or
b) $R^7$ is:
  an amino group having the formula —N($R^b$)($R^c$), wherein each of $R^b$ and $R^c$ is an alkyl group, or —N=N—Het$^1$ wherein Het$^1$ is a heterocyclic group;
$R^{12}$ is:
  a cyano group having the formula —CN,
$R^{15}$ is:
  a cyano group having the formula —CN;
or
c) $R^7$ is:
  an amino group having the formula —N($R^b$)($R^c$), wherein each of $R^b$ and $R^c$ is an alkyl group, or —N=N—Het$^1$ wherein Het$^1$ is a heterocyclic group;
$R^{12}$ is:
  an alkoxy group having the formula —O—$R^h$, wherein $R^h$ is an alkyl group,
$R^{15}$ is:
  a nitro group having the formula —NO$_2$;
or
d) $R^7$ is:
  an amino group having the formula —N($R^b$)($R^c$), wherein each of $R^b$ and $R^c$ is an alkyl group;
$R^{12}$ is:
  H,
  a cyano group having the formula —CN,
  an alkoxy group having the formula —O—$R^b$, wherein $R^b$ is an alkyl group,
  an alkyl group $R^i$, or
  a halogen atom;
$R^{15}$ is:
  a cyano group having the formula —CN;
wherein A is:
  a single bond, or
  a formula selected from the group consisting of:

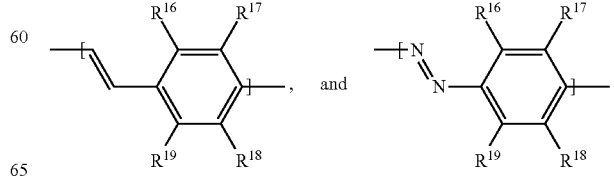

wherein $R^{16}$ is H;

$R^{17}$ is:
  H, or
  an alkoxy group having the formula —O—$R^o$, wherein $R^o$ is an alkyl group;
$R^{18}$ is H;
$R^{19}$ is:
  H, or
  an alkoxy group having the formula —O—$R^p$, wherein $R^p$ is an alkyl group.

2. The electrowetting apparatus of claim 1, wherein the alkyl group of one or more of: $R^a$, $R^b$, $R^c$, $R^d$, $R^e$, $R^f$, $R^g$, $R^h$, $R^i$, $R^j$, $R^k$, $R^o$, or $R^p$ is independently:
  a straight chain alkyl group having 1 to 22 carbon atoms,
  a branched alkyl group having 3 to 22 carbon atoms, or
  a cyclic alkyl group having 5 to 22 carbon atoms.

3. The electrowetting apparatus of claim 1, wherein $R^a$ is:
  a branched alkyl group having 3 to 22 carbon atoms,
  a branched alkyl group having 3 to 8 carbon atoms,
  a branched alkyl group having 8 carbon atoms, or
  a branched alkyl group such that $R^6$ has the formula:

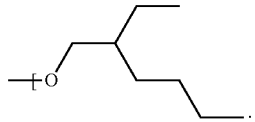

4. The electrowetting apparatus of claim 1, in accordance with b) or c), wherein $R^7$ is the amino group having the formula —N($R^b$)($R^c$), the alkyl group of $R^b$ and $R^c$ are each independently:
  a straight chain alkyl group having 1 to 22 carbon atoms,
  a straight chain alkyl group having 1 to 8 carbon atoms,
  a straight chain alkyl group having 8 carbon atoms,
  a straight chain alkyl group having 6 carbon atoms,
  a straight chain alkyl group having 1 to 5 carbon atoms,
  a straight chain alkyl group having 5 carbon atoms,
  a branched alkyl group having 3 to 22 carbon atoms,
  a branched alkyl group having 3 to 8 carbon atoms,
  a branched alkyl group having 8 carbon atoms,
  a branched alkyl group such that the amino group of $R^7$ has the formula:

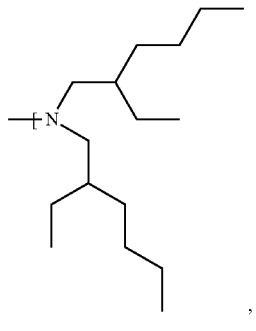

a straight chain alkyl group having 5 carbon atoms, or
  a straight chain alkyl group having 4 carbon atoms.

5. The electrowetting apparatus of claim 1, wherein $R^7$ is —N=N—$Het^1$ where $Het^1$ is a:
  a five membered heterocyclic ring,
  a six membered heterocyclic ring,
  a five membered heterocyclic aromatic ring containing 1 to 3 heteroatoms,
  a six membered heterocyclic aromatic ring containing 1 to 3 heteroatoms,
  a five membered heterocyclic aromatic ring containing 1 heteroatom which is an N atom,
  a six membered heterocyclic aromatic ring containing 1 heteroatom which is an N atom,
  a five membered heterocyclic aromatic ring containing 1 heteroatom which is an N atom, where the —N=N— group is bonded to the heterocyclic aromatic ring at the 2 position relative to the heteroatom,
  a six membered heterocyclic aromatic ring containing 1 heteroatom which is an N atom, where the —N=N— group is bonded to the heterocyclic aromatic ring at the 2 position,
  a five membered heterocyclic aromatic ring containing 1 heteroatom substituted with an alkyl group having 1 to 22 carbon atoms,
  a five membered heterocyclic aromatic ring containing 1 heteroatom substituted with a straight chain alkyl group having 1 to 22 carbon atoms,
  a five membered heterocyclic aromatic ring containing 1 heteroatom substituted with a straight chain alkyl group having 1 to 8 carbon atoms,
  a five membered heterocyclic aromatic ring containing 1 heteroatom substituted with a straight chain alkyl group having 8 carbon atoms,
  a five membered heterocyclic aromatic ring containing 1 heteroatom substituted with a branched alkyl group having 3 to 22 carbon atoms,
  a five membered heterocyclic aromatic ring containing 1 heteroatom substituted with a branched alkyl group having 3 to 8 carbon atoms,
  a five membered heterocyclic aromatic ring containing 1 heteroatom substituted with a branched alkyl group having 8 carbon atoms,
  a five membered heterocyclic aromatic ring containing 1 heteroatom substituted with a branched alkyl group having the formula:

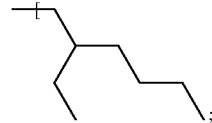

a six membered heterocyclic aromatic ring containing 1 heteroatom substituted with an alkyl group having 1 to 22 carbon atoms,
  a six membered heterocyclic aromatic ring containing 1 heteroatom substituted with a straight chain alkyl group having 1 to 22 carbon atoms,
  a six membered heterocyclic aromatic ring containing 1 heteroatom substituted with a straight chain alkyl group having 1 to 8 carbon atoms,
  a six membered heterocyclic aromatic ring containing 1 heteroatom substituted with a straight chain alkyl group having 8 carbon atoms,
  a six membered heterocyclic aromatic ring containing 1 heteroatom substituted with a branched alkyl group having 3 to 22 carbon atoms,
  a six membered heterocyclic aromatic ring containing 1 heteroatom substituted with a branched alkyl group having 3 to 8 carbon atoms, a six membered heterocyclic aromatic ring containing 1 heteroatom substituted with a branched alkyl group having 8 carbon atoms,
a six membered heterocyclic aromatic ring containing 1 heteroatom substituted with a branched alkyl group having the formula:

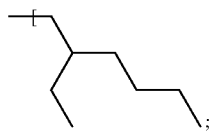

or
a five membered heterocyclic aromatic ring having the formula:

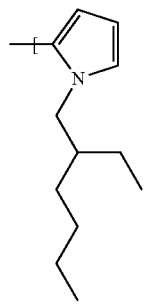

6. The electrowetting apparatus of claim 1, wherein one or more of the following apply:
the alkyl group of $R^d$ is:
a branched alkyl group having 3 to 22 carbon atoms,
a branched alkyl group having 3 to 8 carbon atoms,
a branched alkyl group having 8 carbon atoms, or
a branched alkyl group such that the alkoxy group of $R^9$ has the formula:

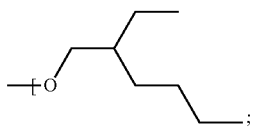

the alkyl group of $R^e$ is:
a branched alkyl group having 3 to 22 carbon atoms,
a branched alkyl group having 3 to 7 carbon atoms,
a branched alkyl group having 7 carbon atoms, or
a branched alkyl group such that the amide group of $R^9$ has the formula:

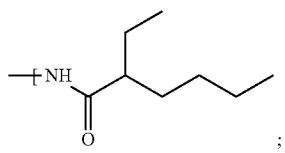

the alkyl group of $R^f$ is:
a branched alkyl group having 3 to 22 carbon atoms,
a branched alkyl group having 3 to 8 carbon atoms,
a branched alkyl group having 8 carbon atoms, or
a branched alkyl group having the formula:

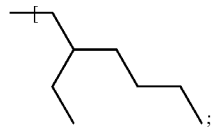

or
the alkyl group of $R^g$ is:
a straight chain alkyl group having 1 to 22 carbon atoms,
a straight chain alkyl group having 2 carbon atoms,
a branched alkyl group having 3 to 22 carbon atoms,
a branched alkyl group having 3 to 8 carbon atoms,
a branched alkyl group having 8 carbon atoms, or
a branched alkyl group having the formula:

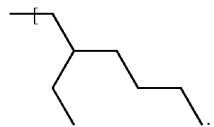

7. The electrowetting apparatus of claim 6, wherein A is:
a single bond, or
has a formula selected from the group consisting of:

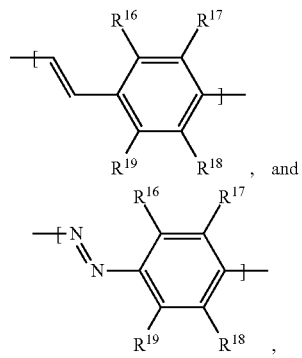

$R^o$ and $R^p$ are each independently:
a branched alkyl group having 3 to 22 carbon atoms,
a branched alkyl group having 3 to 8 carbon atoms,
a branched alkyl group having 8 carbon atoms, or
a branched alkyl group having the formula:

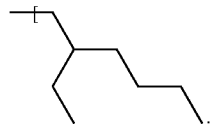

8. The electrowetting apparatus of claim 1, wherein B has:
in accordance with a) or b), a formula where $R^{12}$ is a cyano group having the formula —CN, $R^{13}$ is H, $R^{14}$ is H and $R^{15}$ is a cyano group having the formula —CN,
in accordance with a), a formula wherein $R^{12}$ is H, $R^{13}$ is H, $R^{14}$ is H and $R^{15}$ is a cyano group having the formula —CN, in accordance with c), a formula wherein:
R[12] is an alkoxy group having the formula —O—R[h] wherein R[h] is:
a branched alkyl group having 3 to 22 carbon atoms,
a branched alkyl group having 3 to 8 carbon atoms,
a branched alkyl group having 8 carbon atoms, or
a branched alkyl group having the formula:

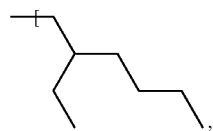

R[13] is H,
R[14] is an alkoxy group having the formula —O—R[k] wherein R[k] is:
a branched alkyl group having 3 to 22 carbon atoms,
a branched alkyl group having 3 to 8 carbon atoms,
a branched alkyl group having 8 carbon atoms, or
a branched alkyl group having the formula:

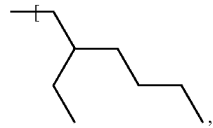

R[15] is a nitro group having the formula —NO$_2$.

9. The electrowetting apparatus of claim 1, the at least one dye compound with the formula according to Formula 1 having the formula:

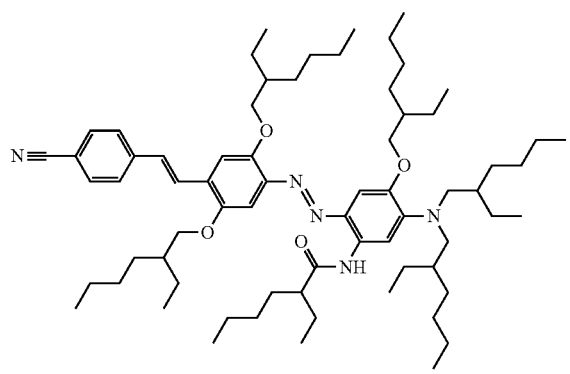

,

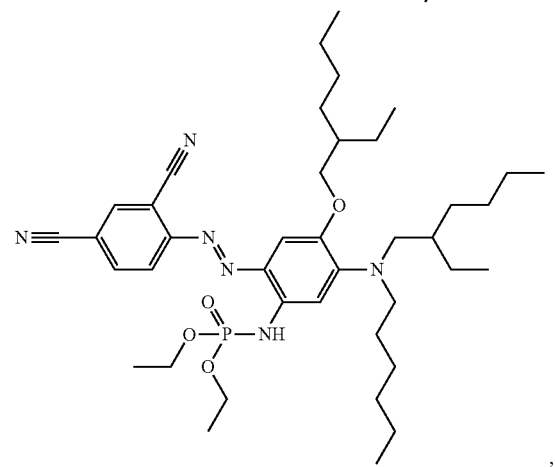

,

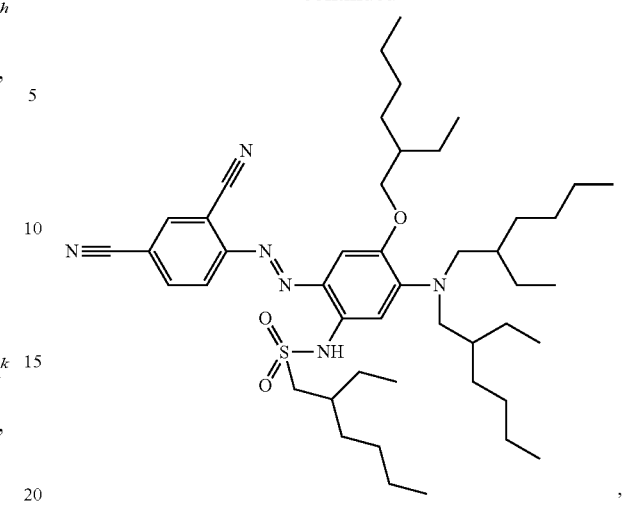

,

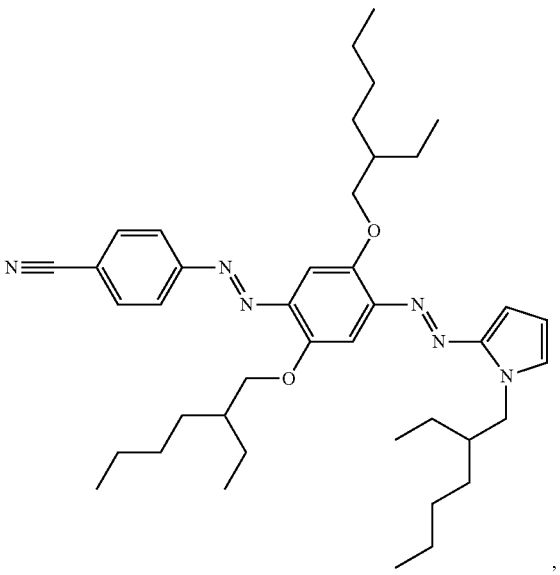

,

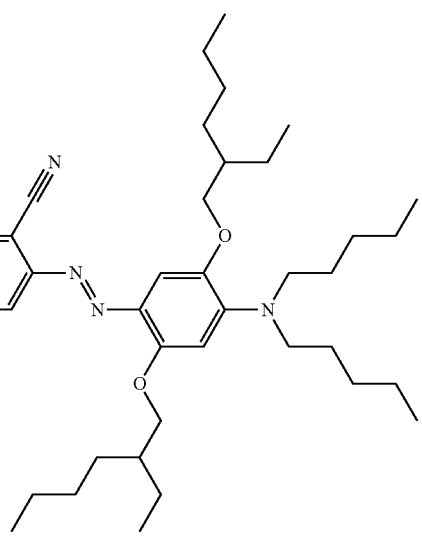

,

-continued

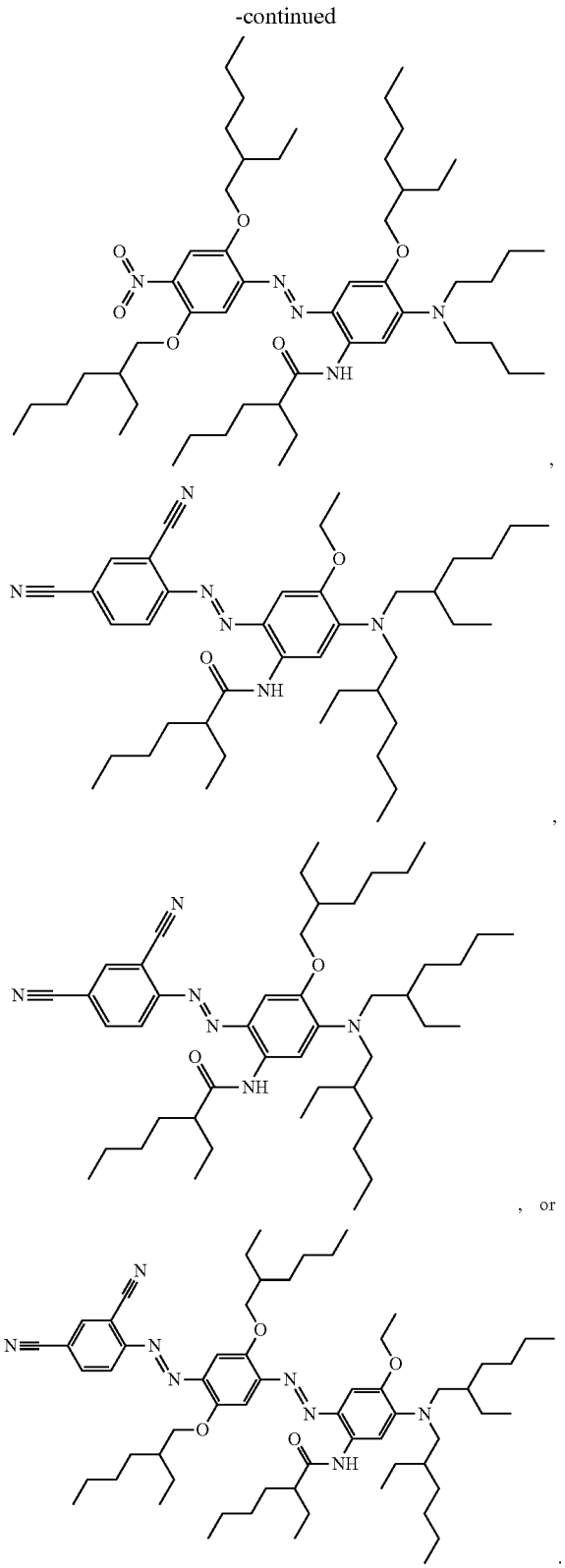
,

, or

.

10. The electrowetting apparatus of claim 1, the fluid further comprising:

(ii) a compound selected from the group consisting of:

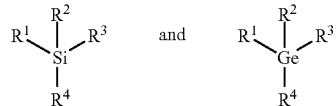

wherein each of $R^1$, $R^2$, $R^3$ and $R^4$ is independently an alkyl group.

11. The electrowetting apparatus of claim 10, wherein the alkyl group of each of $R^1$, $R^2$, $R^3$ and $R^4$ is independently a straight chain alkyl group having the general formula —$(CH_2)_n CH_3$ and n is independently, for each of $R^1$, $R^2$, $R^3$ and $R^4$, in the range of 0 to 7.

12. The electrowetting apparatus according to claim 11, wherein a number of carbon atoms contained by each of $R^1$, $R^2$, $R^3$ and $R^4$ is the same.

13. The electrowetting apparatus according to claim 11, wherein a number of carbon atoms contained by one or more of: $R^1$, $R^2$, $R^3$ or $R^4$ is different from a number of carbon atoms contained by a different one of: $R^1$, $R^2$, $R^3$ or $R^4$.

14. The electrowetting apparatus according to claim 10, wherein the at least one compound comprises a compound with the formula:

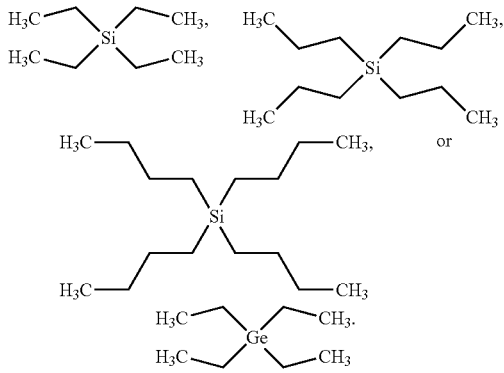

15. The electrowetting apparatus according to claim 10, wherein the compound comprises the following:

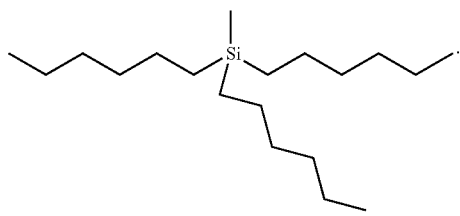 [SMILES: CCCCCC[Si](C)(CCCCCC)CCCCCC]

16. The electrowetting apparatus according to claim 10, wherein:
each of $R^1$, $R^2$, $R^3$ and $R^4$ is independently a branched alkyl group, or
each of $R^1$, $R^2$, $R^3$ and $R^4$ is independently a straight chain alkyl group.

17. The electrowetting apparatus according to claim 10, wherein a total number of carbon atoms contained by all of the alkyl groups $R^1$, $R^2$, $R^3$ and $R^4$ is at most 33 carbon atoms.

18. The electrowetting apparatus according to claim 10, wherein a total number of carbon atoms contained by any one of the alkyl groups $R^1$, $R^2$, $R^3$ and $R^4$ is at most 30 carbon atoms.

19. The electrowetting apparatus according to claim 10, wherein a longest chain of carbon atoms contained by the alkyl group of any of $R^1$, $R^2$, $R^3$ and $R^4$ is at most 24 carbon atoms.

20. The electrowetting apparatus according to claim 10, wherein the alkyl group of each of $R^1$, $R^2$, $R^3$ and $R^4$ is a saturated alkyl group.

21. The electrowetting apparatus according to claim 10, wherein a maximum vapour pressure of the compound of (ii) is about 5 millimeters Hg measured at a temperature of 20 degrees Celsius.

22. The electrowetting apparatus according to claim 10, wherein a dynamic viscosity of the compound of (ii) is in the range of one or more of:

about 0.5 to 37 centiPoise, about 0.5 to 35 centiPoise, about 0.5 to 30 centiPoise, about 0.5 to 25 centiPoise, about 0.5 to 20 centiPoise, about 0.5 to 15 centiPoise, about 0.5 to 10 centiPoise, about 0.5 to 9 centiPoise, about 0.5 to 8 centiPoise, about 0.5 to 7 centiPoise, about 0.5 to 6 centiPoise, about 0.5 to 5.5 centiPoise, about 0.5 to 5.0 centiPoise, about 0.5 to 4.5 centiPoise, about 0.5 to 4.0 centiPoise, about 0.5 to 3.5 centiPoise, or about 0.5 to 3.0 centiPoise, measured at a temperature of 20 degrees Celsius.

23. The electrowetting apparatus according to claim 10, wherein a dynamic viscosity of the compound of (ii) is at most about 37 centiPoise measured at a temperature of 20 degrees Celsius.

24. The electrowetting apparatus according to claim 1, wherein the fluid is a first fluid, and comprising a display element comprising:
 a first support plate;
 a second support plate;
 the first fluid;
 a second fluid immiscible with the first fluid, the first fluid and the second fluid positioned between the first support plate and the second support plate;
 a first electrode in the first support plate; and
 a second electrode in contact with the second fluid.

* * * * *